(12) United States Patent
Kong

(10) Patent No.: US 8,592,181 B2
(45) Date of Patent: Nov. 26, 2013

(54) BRAZZEIN VARIANT HAVING HIGHER SWEETNESS AND METHOD FOR PREPARING MULTI-VARIANT

(75) Inventor: Kwang Hoon Kong, Incheon (KR)

(73) Assignee: Chung-Ang University Industry-Academy Cooperation Foundation, Seoul (KR)

( * ) Notice: Subject to any disclaimer, the term of this patent is extended or adjusted under 35 U.S.C. 154(b) by 0 days.

(21) Appl. No.: 13/392,378

(22) PCT Filed: Aug. 28, 2009

(86) PCT No.: PCT/KR2009/004855
§ 371 (c)(1),
(2), (4) Date: Feb. 24, 2012

(87) PCT Pub. No.: WO2011/025077
PCT Pub. Date: Mar. 3, 2011

(65) Prior Publication Data
US 2012/0220756 A1    Aug. 30, 2012

(51) Int. Cl.
| | |
|---|---|
| C12P 21/04 | (2006.01) |
| C12N 15/00 | (2006.01) |
| C12N 1/20 | (2006.01) |
| C07K 14/00 | (2006.01) |
| C07H 21/02 | (2006.01) |
| A23L 1/236 | (2006.01) |
| A23J 1/00 | (2006.01) |

(52) U.S. Cl.
USPC ......... 435/71.2; 530/300; 530/324; 536/23.1; 435/320.1; 435/252.33; 426/548; 426/656

(58) Field of Classification Search
None
See application file for complete search history.

(56) References Cited

U.S. PATENT DOCUMENTS 7,153,535 B2   12/2006   Jin et al.

FOREIGN PATENT DOCUMENTS

| KR | 10-0809100 B1 * | 3/2008 |
|---|---|---|
| KR | 10-2009-0050525 | 5/2009 |
| KR | 10-2009-0093470 | 9/2009 |

OTHER PUBLICATIONS

Voet et al., "Biochemistry", Second Edition, John Wiley and Sons, New York, 1995, p. 60.*
Machine translation of KR 10-0809100 B1, obtained from Korean Intellectual Property Office on Feb. 28, 2013, 14 pages.*
Machine translation of KR 10-2009-0050525, obtained from Korean Intellectual Property Office on Feb. 28, 2013, 10 pages.*
Lee et al. "Design and Efficient Soluble Expression of a Sweet Protein, Brazzein and Minor-Form Mutant", Bull. Korean Chem. Soc. 31:3830-3833, 2010.*
Kong et al., "Effects of mutations on functional properties of the small sweet protein brazzein", FEBS J. vol. 274, Issue Supplement S1, Abstract E5-5, p. 260, 2007.*
Assadi et al., "Sweetness determinant sites of brazzein, a small, heat-stable, sweet-tasting protein.", Apr. 15, 2000, Archives of Biochemistry and Biophysics 376(2): 259-265.
Jin et al., "Critical regions for the sweetness of brazzein", May 2, 2003, FEBS Letters 544: 33-37.
Zhao et al., "Probing the sweet determinants of brazzein: Wild-type brazzein and a tasteless bariant, brazzein-ins(R18a-118b), exhibit different pH-dependent NMR chemical shifts", 2005, Biochemical and Biophysical Research Communications 335: 256-263.
International Search Report mailed May 31, 2010 for corresponding International Patent Application No. PCT/KR2009/004855.

* cited by examiner

Primary Examiner — David J Steadman
(74) Attorney, Agent, or Firm — Swanson & Bratschun, L.L.C.

(57) ABSTRACT

Novel brazzein variants having higher sweetness and the use thereof are provided. The brazzein variants or multi-variants have higher sweetness than a wild-type brazzein protein. Also, a method of preparing the brazzein variants and a food composition for enhancing a sugar content including the same are provided. The brazzein variants or multi-variants have higher sweetness at least twice that of a conventional brazzein protein, and show equivalent properties such as thermal and pH stabilities and high water solubility compared to the conventional brazzein protein. Therefore, a smaller amount of brazzein variants can be used together with a greater amount of other sweeteners such as sucrose, and can be replaced with the other sweeteners. So, the brazzein variants can be widely used as an additive in manufacture of food products.

9 Claims, 6 Drawing Sheets

Fig. 2
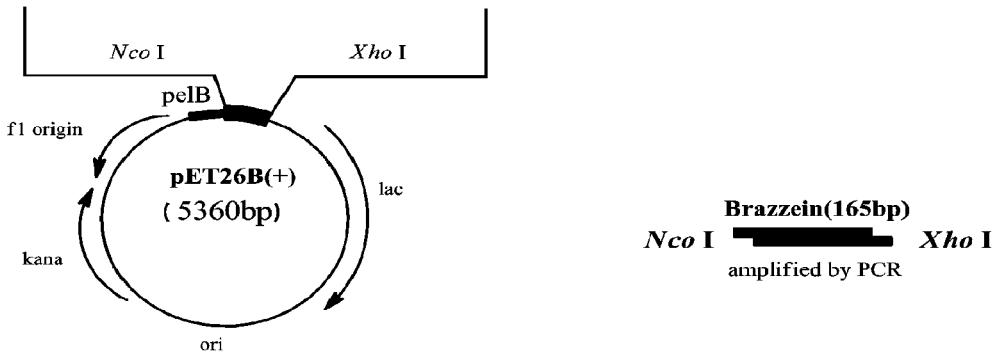
1. Double Digesetion(*Nco* I, *Xho* I)
2. Ligation
3. Transformation(BL21 Star(DE3))
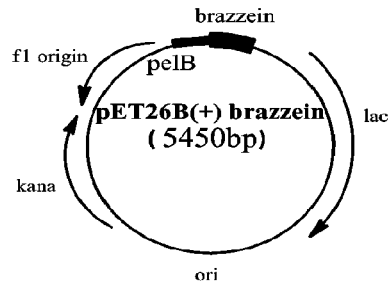
Site-direted Mutagenesis
pET26B(+) Brazzein(Met-)

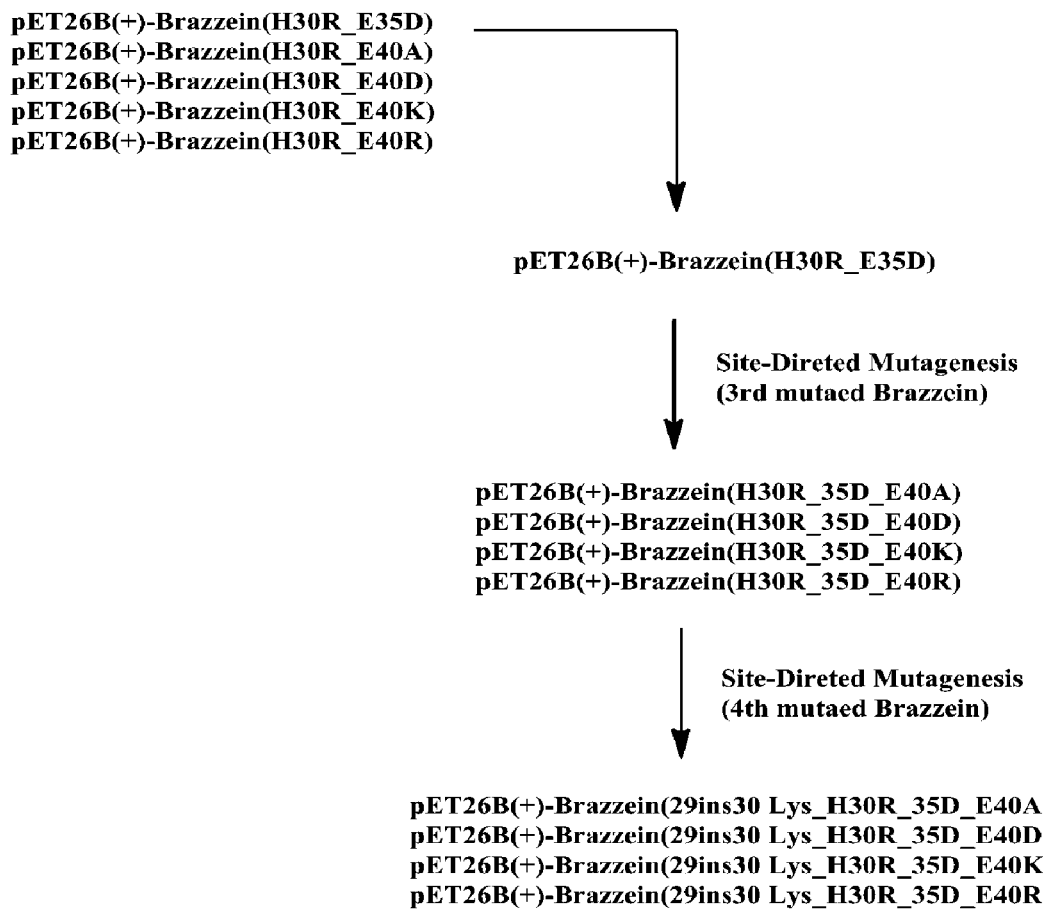
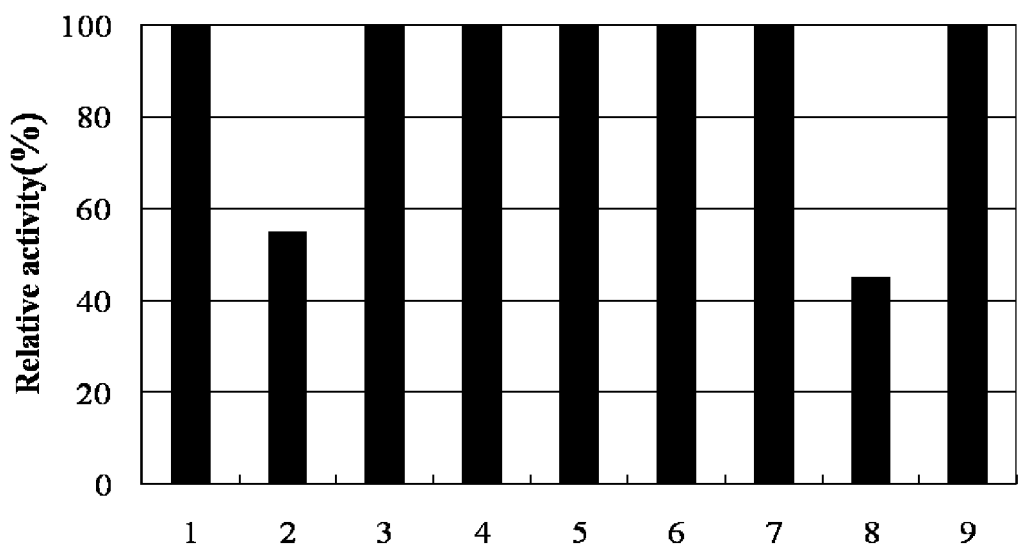

Fig. 6
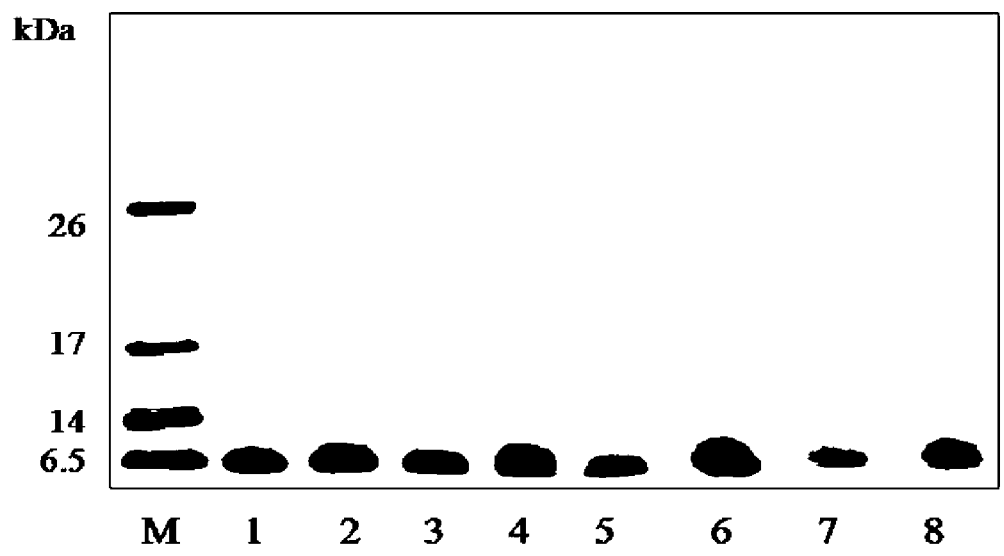
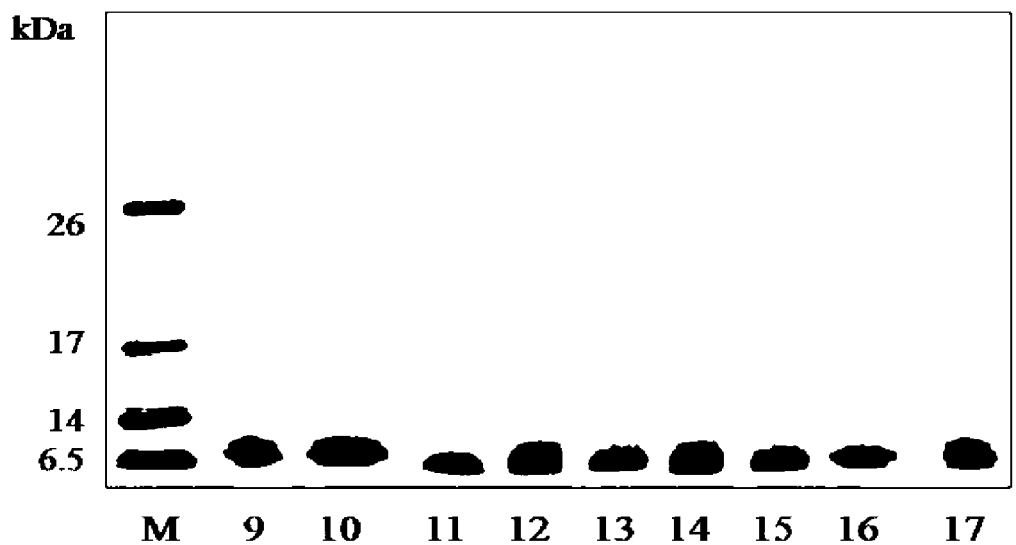

SEQUENCE LISTING

<160> NUMBER OF SEQ ID NOS: 163

<210> SEQ ID NO 1
<211> LENGTH: 228
<212> TYPE: DNA
<213> ORGANISM: Artificial sequence
<220> FEATURE:
<223> OTHER INFORMATION: E. coli pelB + Brazzein gene (Met-)

<400> SEQUENCE: 1

```
atgaaatacc tgctgccgac cgctgctgct ggtctgctgc tcctcgctgc ccagccggcg      60
atggccgata agtgcaagaa ggtttacgaa aattacccag tttctaagtg ccaacttgct     120
aatcaatgca attacgattg caagcttgat aagcatgcta gatctggaga atgcttttac     180
gatgaaaaga gaaatcttca atgcatttgc gattactgcg aatactaa                  228
```

<210> SEQ ID NO 2
<211> LENGTH: 15
<212> TYPE: DNA
<213> ORGANISM: Artificial Sequence
<220> FEATURE:
<223> OTHER INFORMATION: synthesized

<400> SEQUENCE: 2

```
tgcaaggctg tttac                                                       15
```

<210> SEQ ID NO 3
<211> LENGTH: 15
<212> TYPE: DNA
<213> ORGANISM: Artificial Sequence
<220> FEATURE:
<223> OTHER INFORMATION: synthesized

<400> SEQUENCE: 3

```
tgcaaggacg tttac                                                       15
```

<210> SEQ ID NO 4
<211> LENGTH: 15
<212> TYPE: DNA
<213> ORGANISM: Artificial Sequence
<220> FEATURE:
<223> OTHER INFORMATION: synthesized

<400> SEQUENCE: 4

```
tgcaaggaag tttac                                                       15
```

<210> SEQ ID NO 5
<211> LENGTH: 15
<212> TYPE: DNA
<213> ORGANISM: Artificial Sequence
<220> FEATURE:
<223> OTHER INFORMATION: synthesized

<400> SEQUENCE: 5

```
tgcaagcacg tttac                                                       15
```

<210> SEQ ID NO 6
<211> LENGTH: 15
<212> TYPE: DNA
<213> ORGANISM: Artificial Sequence
<220> FEATURE:
<223> OTHER INFORMATION: synthesized

<400> SEQUENCE: 6
tgcaagcgtg tttac                                                        15

<210> SEQ ID NO 7
<211> LENGTH: 15
<212> TYPE: DNA
<213> ORGANISM: Artificial Sequence
<220> FEATURE:
<223> OTHER INFORMATION: synthesized

<400> SEQUENCE: 7
aagcttgcta agcat                                                        15

<210> SEQ ID NO 8
<211> LENGTH: 15
<212> TYPE: DNA
<213> ORGANISM: Artificial Sequence
<220> FEATURE:
<223> OTHER INFORMATION: synthesized

<400> SEQUENCE: 8
aagcttcaca agcat                                                        15

<210> SEQ ID NO 9
<211> LENGTH: 15
<212> TYPE: DNA
<213> ORGANISM: Artificial Sequence
<220> FEATURE:
<223> OTHER INFORMATION: synthesized

<400> SEQUENCE: 9
aagcttaaaa agcat                                                        15

<210> SEQ ID NO 10
<211> LENGTH: 15
<212> TYPE: DNA
<213> ORGANISM: Artificial Sequence
<220> FEATURE:
<223> OTHER INFORMATION: synthesized

<400> SEQUENCE: 10
aagcttcgta agcat                                                        15

<210> SEQ ID NO 11
<211> LENGTH: 15
<212> TYPE: DNA
<213> ORGANISM: Artificial Sequence
<220> FEATURE:
<223> OTHER INFORMATION: synthesized

<400> SEQUENCE: 11
aagcttgaaa agcat                                                        15

<210> SEQ ID NO 12
<211> LENGTH: 15
<212> TYPE: DNA
<213> ORGANISM: Artificial Sequence
<220> FEATURE:
<223> OTHER INFORMATION: synthesized

<400> SEQUENCE: 12
cttgatgctc atgct                                                        15

<210> SEQ ID NO 13
<211> LENGTH: 15
<212> TYPE: DNA
<213> ORGANISM: Artificial Sequence
<220> FEATURE:

```
<223> OTHER INFORMATION: synthesized

<400> SEQUENCE: 13
cttgatcgtc atgct                                                        15

<210> SEQ ID NO 14
<211> LENGTH: 15
<212> TYPE: DNA
<213> ORGANISM: Artificial Sequence
<220> FEATURE:
<223> OTHER INFORMATION: synthesized

<400> SEQUENCE: 14
cttgatcgcc atgct                                                        15

<210> SEQ ID NO 15
<211> LENGTH: 15
<212> TYPE: DNA
<213> ORGANISM: Artificial Sequence
<220> FEATURE:
<223> OTHER INFORMATION: synthesized

<400> SEQUENCE: 15
cttgatgacc atgct                                                        15

<210> SEQ ID NO 16
<211> LENGTH: 15
<212> TYPE: DNA
<213> ORGANISM: Artificial Sequence
<220> FEATURE:
<223> OTHER INFORMATION: synthesized

<400> SEQUENCE: 16
cttgatgaac atgct                                                        15

<210> SEQ ID NO 17
<211> LENGTH: 15
<212> TYPE: DNA
<213> ORGANISM: Artificial Sequence
<220> FEATURE:
<223> OTHER INFORMATION: synthesized

<400> SEQUENCE: 17
gataaggctg ctcga                                                        15

<210> SEQ ID NO 18
<211> LENGTH: 15
<212> TYPE: DNA
<213> ORGANISM: Artificial Sequence
<220> FEATURE:
<223> OTHER INFORMATION: synthesized

<400> SEQUENCE: 18
gataagaaag ctcga                                                        15

<210> SEQ ID NO 19
<211> LENGTH: 15
<212> TYPE: DNA
<213> ORGANISM: Artificial Sequence
<220> FEATURE:
<223> OTHER INFORMATION: synthesized

<400> SEQUENCE: 19
gataagcgtg ctcga                                                        15

<210> SEQ ID NO 20
```

```
<211> LENGTH: 15
<212> TYPE: DNA
<213> ORGANISM: Artificial Sequence
<220> FEATURE:
<223> OTHER INFORMATION: synthesized

<400> SEQUENCE: 20
gataaggacg ctcga                                                      15

<210> SEQ ID NO 21
<211> LENGTH: 15
<212> TYPE: DNA
<213> ORGANISM: Artificial Sequence
<220> FEATURE:
<223> OTHER INFORMATION: synthesized

<400> SEQUENCE: 21
gataaggaag ctcga                                                      15

<210> SEQ ID NO 22
<211> LENGTH: 15
<212> TYPE: DNA
<213> ORGANISM: Artificial Sequence
<220> FEATURE:
<223> OTHER INFORMATION: synthesized

<400> SEQUENCE: 22
catgctgctt ctgga                                                      15

<210> SEQ ID NO 23
<211> LENGTH: 15
<212> TYPE: DNA
<213> ORGANISM: Artificial Sequence
<220> FEATURE:
<223> OTHER INFORMATION: synthesized

<400> SEQUENCE: 23
catgctaaat ctgga                                                      15

<210> SEQ ID NO 24
<211> LENGTH: 15
<212> TYPE: DNA
<213> ORGANISM: Artificial Sequence
<220> FEATURE:
<223> OTHER INFORMATION: synthesized

<400> SEQUENCE: 24
catgctcgct ctgga                                                      15

<210> SEQ ID NO 25
<211> LENGTH: 15
<212> TYPE: DNA
<213> ORGANISM: Artificial Sequence
<220> FEATURE:
<223> OTHER INFORMATION: synthesized

<400> SEQUENCE: 25
catgctgact ctgga                                                      15

<210> SEQ ID NO 26
<211> LENGTH: 15
<212> TYPE: DNA
<213> ORGANISM: Artificial Sequence
<220> FEATURE:
<223> OTHER INFORMATION: synthesized

<400> SEQUENCE: 26
```
catgctgaat ctgga 15

<210> SEQ ID NO 27
<211> LENGTH: 15
<212> TYPE: DNA
<213> ORGANISM: Artificial Sequence
<220> FEATURE:
<223> OTHER INFORMATION: synthesized

<400> SEQUENCE: 27
tctggagctt gcttt 15

<210> SEQ ID NO 28
<211> LENGTH: 15
<212> TYPE: DNA
<213> ORGANISM: Artificial Sequence
<220> FEATURE:
<223> OTHER INFORMATION: synthesized

<400> SEQUENCE: 28
tctggagact gcttt 15

<210> SEQ ID NO 29
<211> LENGTH: 15
<212> TYPE: DNA
<213> ORGANISM: Artificial Sequence
<220> FEATURE:
<223> OTHER INFORMATION: synthesized

<400> SEQUENCE: 29
tctggaaaat gcttt 15

<210> SEQ ID NO 30
<211> LENGTH: 15
<212> TYPE: DNA
<213> ORGANISM: Artificial Sequence
<220> FEATURE:
<223> OTHER INFORMATION: synthesized

<400> SEQUENCE: 30
tctggacgct gcttt 15

<210> SEQ ID NO 31
<211> LENGTH: 15
<212> TYPE: DNA
<213> ORGANISM: Artificial Sequence
<220> FEATURE:
<223> OTHER INFORMATION: synthesized

<400> SEQUENCE: 31
tctggacgtt gcttt 15

<210> SEQ ID NO 32
<211> LENGTH: 15
<212> TYPE: DNA
<213> ORGANISM: Artificial Sequence
<220> FEATURE:
<223> OTHER INFORMATION: synthesized

<400> SEQUENCE: 32
tacgatgcta agaga 15

<210> SEQ ID NO 33
<211> LENGTH: 15
<212> TYPE: DNA
<213> ORGANISM: Artificial Sequence
<220> FEATURE:

<223> OTHER INFORMATION: synthesized

<400> SEQUENCE: 33
tacgatgaca agaga                                              15

<210> SEQ ID NO 34
<211> LENGTH: 15
<212> TYPE: DNA
<213> ORGANISM: Artificial Sequence
<220> FEATURE:
<223> OTHER INFORMATION: synthesized

<400> SEQUENCE: 34
tacgataaaa agaga                                              15

<210> SEQ ID NO 35
<211> LENGTH: 15
<212> TYPE: DNA
<213> ORGANISM: Artificial Sequence
<220> FEATURE:
<223> OTHER INFORMATION: synthesized

<400> SEQUENCE: 35
tacgatcgca agaga                                              15

<210> SEQ ID NO 36
<211> LENGTH: 15
<212> TYPE: DNA
<213> ORGANISM: Artificial Sequence
<220> FEATURE:
<223> OTHER INFORMATION: synthesized

<400> SEQUENCE: 36
tacgatcgta agaga                                              15

<210> SEQ ID NO 37
<211> LENGTH: 15
<212> TYPE: DNA
<213> ORGANISM: Artificial Sequence
<220> FEATURE:
<223> OTHER INFORMATION: synthesized

<400> SEQUENCE: 37
gaaaaggcta atctt                                              15

<210> SEQ ID NO 38
<211> LENGTH: 15
<212> TYPE: DNA
<213> ORGANISM: Artificial Sequence
<220> FEATURE:
<223> OTHER INFORMATION: synthesized

<400> SEQUENCE: 38
gaaaaggaca atctt                                              15

<210> SEQ ID NO 39
<211> LENGTH: 15
<212> TYPE: DNA
<213> ORGANISM: Artificial Sequence
<220> FEATURE:
<223> OTHER INFORMATION: synthesized

<400> SEQUENCE: 39
gaaaagcgca atctt                                              15

<210> SEQ ID NO 40

-continued

```
<211> LENGTH: 15
<212> TYPE: DNA
<213> ORGANISM: Artificial Sequence
<220> FEATURE:
<223> OTHER INFORMATION: synthesized

<400> SEQUENCE: 40
gaaaaggaca atctt                                                        15

<210> SEQ ID NO 41
<211> LENGTH: 15
<212> TYPE: DNA
<213> ORGANISM: Artificial Sequence
<220> FEATURE:
<223> OTHER INFORMATION: synthesized

<400> SEQUENCE: 41
gaaaaggaaa atctt                                                        15

<210> SEQ ID NO 42
<211> LENGTH: 228
<212> TYPE: DNA
<213> ORGANISM: Artificial Sequence
<220> FEATURE:
<223> OTHER INFORMATION: E. coli pelB +Brazzein(K5A) gene

<400> SEQUENCE: 42
atgaaatacc tgctgccgac cgctgctgct ggtctgctgc tcctcgctgc ccagccggcg        60
atggccgata agtgcaaagc tgtttacgaa aattacccag tttctaagtg ccaacttgct       120
aatcaatgca attacgattg caagcttgat aagcgtgcta gatctggaga ctgcttttac       180
gatcgtaaga gaaatcttca atgcatttgc gattactgcg aatactaa                    228

<210> SEQ ID NO 43
<211> LENGTH: 228
<212> TYPE: DNA
<213> ORGANISM: Artificial Sequence
<220> FEATURE:
<223> OTHER INFORMATION: E. coli pelB +Brazzein(K5D) gene

<400> SEQUENCE: 43
atgaaatacc tgctgccgac cgctgctgct ggtctgctgc tcctcgctgc ccagccggcg        60
atggccgata agtgcaaaga cgtttacgaa aattacccag tttctaagtg ccaacttgct       120
aatcaatgca attacgattg caagcttgat aagcgtgcta gatctggaga ctgcttttac       180
gatcgtaaga gaaatcttca atgcatttgc gattactgcg aatactaa                    228

<210> SEQ ID NO 44
<211> LENGTH: 228
<212> TYPE: DNA
<213> ORGANISM: Artificial Sequence
<220> FEATURE:
<223> OTHER INFORMATION: E. coli pelB +Brazzein(K5E) gene

<400> SEQUENCE: 44
atgaaatacc tgctgccgac cgctgctgct ggtctgctgc tcctcgctgc ccagccggcg        60
atggccgata agtgcaaaga agtttacgaa aattacccag tttctaagtg ccaacttgct       120
aatcaatgca attacgattg caagcttgat aagcgtgcta gatctggaga ctgcttttac       180
gatcgtaaga gaaatcttca atgcatttgc gattactgcg aatactaa                    228

<210> SEQ ID NO 45
<211> LENGTH: 228
<212> TYPE: DNA
```

<213> ORGANISM: Artificial Sequence
<220> FEATURE:
<223> OTHER INFORMATION: E. coli pelB +Brazzein(K5H) gene

<400> SEQUENCE: 45

```
atgaaatacc tgctgccgac cgctgctgct ggtctgctgc tcctcgctgc ccagccggcg      60
atggccgata agtgcaaaca cgtttacgaa aattacccag tttctaagtg ccaacttgct     120
aatcaatgca attacgattg caagcttgat aagcgtgcta gatctggaga ctgcttttac     180
gatcgtaaga gaaatcttca atgcatttgc gattactgcg aatactaa                  228
```

<210> SEQ ID NO 46
<211> LENGTH: 228
<212> TYPE: DNA
<213> ORGANISM: Artificial Sequence
<220> FEATURE:
<223> OTHER INFORMATION: E. coli pelB +Brazzein(K5R) gene

<400> SEQUENCE: 46

```
atgaaatacc tgctgccgac cgctgctgct ggtctgctgc tcctcgctgc ccagccggcg      60
atggccgata agtgcaaacg tgtttacgaa aattacccag tttctaagtg ccaacttgct     120
aatcaatgca attacgattg caagcttgat aagcgtgcta gatctggaga ctgcttttac     180
gatcgtaaga gaaatcttca atgcatttgc gattactgcg aatactaa                  228
```

<210> SEQ ID NO 47
<211> LENGTH: 228
<212> TYPE: DNA
<213> ORGANISM: Artificial Sequence
<220> FEATURE:
<223> OTHER INFORMATION: E. coli pelB +Brazzein(D28A) gene

<400> SEQUENCE: 47

```
atgaaatacc tgctgccgac cgctgctgct ggtctgctgc tcctcgctgc ccagccggcg      60
atggccgata agtgcaagaa ggtttacgaa aattacccag tttctaagtg ccaacttgct     120
aatcaatgca attacgattg caagcttgct aagcatgcta gatctggaga atgcttttac     180
gatgaaaaga gaaatcttca atgcatttgc gattactgcg aatactaa                  228
```

<210> SEQ ID NO 48
<211> LENGTH: 228
<212> TYPE: DNA
<213> ORGANISM: Artificial Sequence
<220> FEATURE:
<223> OTHER INFORMATION: E. coli pelB +Brazzein(D28H) gene

<400> SEQUENCE: 48

```
atgaaatacc tgctgccgac cgctgctgct ggtctgctgc tcctcgctgc ccagccggcg      60
atggccgata agtgcaaacg tgtttacgaa aattacccag tttctaagtg ccaacttgct     120
aatcaatgca attacgattg caagcttgct aagcgtgcta gatctggaga ctgcttttac     180
gatcgtaaga gaaatcttca atgcatttgc gattactgcg aatactaa                  228
```

<210> SEQ ID NO 49
<211> LENGTH: 228
<212> TYPE: DNA
<213> ORGANISM: Artificial Sequence
<220> FEATURE:
<223> OTHER INFORMATION: E. coli pelB +Brazzein(D28K) gene

<400> SEQUENCE: 49

```
atgaaatacc tgctgccgac cgctgctgct ggtctgctgc tcctcgctgc ccagccggcg      60
```

```
atggccgata agtgcaagaa ggtttacgaa aattacccag tttctaagtg ccaacttgct        120
aatcaatgca attacgattg caagcttaaa aagcatgcta gatctggaga atgcttttac        180
gatgaaaaga gaaatcttca atgcatttgc gattactgcg aatactaa                    228
```

<210> SEQ ID NO 50
<211> LENGTH: 228
<212> TYPE: DNA
<213> ORGANISM: Artificial Sequence
<220> FEATURE:
<223> OTHER INFORMATION: E. coli pelB +Brazzein(D28R) gene

<400> SEQUENCE: 50

```
atgaaatacc tgctgccgac cgctgctgct ggtctgctgc tcctcgctgc ccagccggcg        60
atggccgata agtgcaagaa ggtttacgaa aattacccag tttctaagtg ccaacttgct       120
aatcaatgca attacgattg caagcttcgt aagcatgcta gatctggaga atgcttttac       180
gatgaaaaga gaaatcttca atgcatttgc gattactgcg aatactaa                   228
```

<210> SEQ ID NO 51
<211> LENGTH: 228
<212> TYPE: DNA
<213> ORGANISM: Artificial Sequence
<220> FEATURE:
<223> OTHER INFORMATION: E. coli pelB +Brazzein(D28E) gene

<400> SEQUENCE: 51

```
atgaaatacc tgctgccgac cgctgctgct ggtctgctgc tcctcgctgc ccagccggcg        60
atggccgata agtgcaagaa ggtttacgaa aattacccag tttctaagtg ccaacttgct       120
aatcaatgca attacgattg caagcttgaa aagcatgcta gatctggaga atgcttttac       180
gatgaaaaga gaaatcttca atgcatttgc gattactgcg aatactaa                   228
```

<210> SEQ ID NO 52
<211> LENGTH: 228
<212> TYPE: DNA
<213> ORGANISM: Artificial Sequence
<220> FEATURE:
<223> OTHER INFORMATION: E. coli pelB +Brazzein(K29A) gene

<400> SEQUENCE: 52

```
atgaaatacc tgctgccgac cgctgctgct ggtctgctgc tcctcgctgc ccagccggcg        60
atggccgata agtgcaagaa ggtttacgaa aattacccag tttctaagtg ccaacttgct       120
aatcaatgca attacgattg caagcttgat gctcatgcta gatctggaga atgcttttac       180
gatgaaaaga gaaatcttca atgcatttgc gattactgcg aatactaa                   228
```

<210> SEQ ID NO 53
<211> LENGTH: 228
<212> TYPE: DNA
<213> ORGANISM: Artificial Sequence
<220> FEATURE:
<223> OTHER INFORMATION: E. coli pelB +Brazzein(K29R) gene

<400> SEQUENCE: 53

```
atgaaatacc tgctgccgac cgctgctgct ggtctgctgc tcctcgctgc ccagccggcg        60
atggccgata agtgcaagaa ggtttacgaa aattacccag tttctaagtg ccaacttgct       120
aatcaatgca attacgattg caagcttgat cgtcatgcta gatctggaga atgcttttac       180
gatgaaaaga gaaatcttca atgcatttgc gattactgcg aatactaa                   228
```

<210> SEQ ID NO 54

```
<211> LENGTH: 228
<212> TYPE: DNA
<213> ORGANISM: Artificial Sequence
<220> FEATURE:
<223> OTHER INFORMATION: E. coli pelB +Brazzein(K29H) gene

<400> SEQUENCE: 54
atgaaatacc tgctgccgac cgctgctgct ggtctgctgc tcctcgctgc ccagccggcg      60
atggccgata agtgcaagaa ggtttacgaa aattacccag tttctaagtg ccaacttgct     120
aatcaatgca attacgattg caagcttgat cgccatgcta gatctggaga atgcttttac     180
gatgaaaaga gaaatcttca atgcatttgc gattactgcg aatactaa                  228

<210> SEQ ID NO 55
<211> LENGTH: 228
<212> TYPE: DNA
<213> ORGANISM: Artificial Sequence
<220> FEATURE:
<223> OTHER INFORMATION: E. coli pelB +Brazzein(K29D) gene

<400> SEQUENCE: 55
atgaaatacc tgctgccgac cgctgctgct ggtctgctgc tcctcgctgc ccagccggcg      60
atggccgata agtgcaagaa ggtttacgaa aattacccag tttctaagtg ccaacttgct     120
aatcaatgca attacgattg caagcttgat gaccatgcta gatctggaga atgcttttac     180
gatgaaaaga gaaatcttca atgcatttgc gattactgcg aatactaa                  228

<210> SEQ ID NO 56
<211> LENGTH: 228
<212> TYPE: DNA
<213> ORGANISM: Artificial Sequence
<220> FEATURE:
<223> OTHER INFORMATION: E. coli pelB +Brazzein(K29E) gene

<400> SEQUENCE: 56
atgaaatacc tgctgccgac cgctgctgct ggtctgctgc tcctcgctgc ccagccggcg      60
atggccgata agtgcaagaa ggtttacgaa aattacccag tttctaagtg ccaacttgct     120
aatcaatgca attacgattg caagcttgat gaacatgcta gatctggaga atgcttttac     180
gatgaaaaga gaaatcttca atgcatttgc gattactgcg aatactaa                  228

<210> SEQ ID NO 57
<211> LENGTH: 228
<212> TYPE: DNA
<213> ORGANISM: Artificial Sequence
<220> FEATURE:
<223> OTHER INFORMATION: E. coli pelB +Brazzein(H30A) gene

<400> SEQUENCE: 57
atgaaatacc tgctgccgac cgctgctgct ggtctgctgc tcctcgctgc ccagccggcg      60
atggccgata agtgcaagaa ggtttacgaa aattacccag tttctaagtg ccaacttgct     120
aatcaatgca attacgattg caagcttgat aaggctgcta gatctggaga atgcttttac     180
gatgaaaaga gaaatcttca atgcatttgc gattactgcg aatactaa                  228

<210> SEQ ID NO 58
<211> LENGTH: 228
<212> TYPE: DNA
<213> ORGANISM: Artificial Sequence
<220> FEATURE:
<223> OTHER INFORMATION: E. coli pelB +Brazzein(H30K) gene

<400> SEQUENCE: 58
```

```
atgaaatacc tgctgccgac cgctgctgct ggtctgctgc tcctcgctgc ccagccggcg    60
atggccgata agtgcaagaa ggtttacgaa aattacccag tttctaagtg ccaacttgct    120
aatcaatgca attacgattg caagcttgat aagcgtgcta gatctggaga atgcttttac    180
gatgaaaaga gaaatcttca atgcatttgc gattactgcg aatactaa              228
```

```
<210> SEQ ID NO 59
<211> LENGTH: 228
<212> TYPE: DNA
<213> ORGANISM: Artificial Sequence
<220> FEATURE:
<223> OTHER INFORMATION: E. coli pelB +Brazzein(H30R) gene

<400> SEQUENCE: 59
atgaaatacc tgctgccgac cgctgctgct ggtctgctgc tcctcgctgc ccagccggcg    60
atggccgata agtgcaagaa ggtttacgaa aattacccag tttctaagtg ccaacttgct    120
aatcaatgca attacgattg caagcttgat aagcgtgcta gatctggaga atgcttttac    180
gatgaaaaga gaaatcttca atgcatttgc gattactgcg aatactaa              228
```

```
<210> SEQ ID NO 60
<211> LENGTH: 228
<212> TYPE: DNA
<213> ORGANISM: Artificial Sequence
<220> FEATURE:
<223> OTHER INFORMATION: E. coli pelB +Brazzein(H30D) gene

<400> SEQUENCE: 60
atgaaatacc tgctgccgac cgctgctgct ggtctgctgc tcctcgctgc ccagccggcg    60
atggccgata agtgcaagaa ggtttacgaa aattacccag tttctaagtg ccaacttgct    120
aatcaatgca attacgattg caagcttgat aaggacgcta gatctggaga atgcttttac    180
gatgaaaaga gaaatcttca atgcatttgc gattactgcg aatactaa              228
```

```
<210> SEQ ID NO 61
<211> LENGTH: 228
<212> TYPE: DNA
<213> ORGANISM: Artificial Sequence
<220> FEATURE:
<223> OTHER INFORMATION: E. coli pelB +Brazzein(H30E) gene

<400> SEQUENCE: 61
atgaaatacc tgctgccgac cgctgctgct ggtctgctgc tcctcgctgc ccagccggcg    60
atggccgata agtgcaagaa ggtttacgaa aattacccag tttctaagtg ccaacttgct    120
aatcaatgca attacgattg caagcttgat aaggaagcta gatctggaga atgcttttac    180
gatgaaaaga gaaatcttca atgcatttgc gattactgcg aatactaa              228
```

```
<210> SEQ ID NO 62
<211> LENGTH: 228
<212> TYPE: DNA
<213> ORGANISM: Artificial Sequence
<220> FEATURE:
<223> OTHER INFORMATION: E. coli pelB +Brazzein(R32A) gene

<400> SEQUENCE: 62
atgaaatacc tgctgccgac cgctgctgct ggtctgctgc tcctcgctgc ccagccggcg    60
atggccgata agtgcaagaa ggtttacgaa aattacccag tttctaagtg ccaacttgct    120
aatcaatgca attacgattg caagcttgat aagcatgctg cttctggaga atgcttttac    180
gatgaaaaga gaaatcttca atgcatttgc gattactgcg aatactaa              228
```

<210> SEQ ID NO 63
<211> LENGTH: 228
<212> TYPE: DNA
<213> ORGANISM: Artificial Sequence
<220> FEATURE:
<223> OTHER INFORMATION: E. coli pelB +Brazzein(R32K) gene

<400> SEQUENCE: 63

```
atgaaatacc tgctgccgac cgctgctgct ggtctgctgc tcctcgctgc ccagccggcg      60
atggccgata agtgcaagaa ggtttacgaa aattacccag tttctaagtg ccaacttgct     120
aatcaatgca attacgattg caagcttgat aagcatgcta atctggaga atgcttttac     180 gatgaaaaga gaaatcttca atgcatttgc gattactgcg aatactaa                 228
```

<210> SEQ ID NO 64
<211> LENGTH: 228
<212> TYPE: DNA
<213> ORGANISM: Artificial Sequence
<220> FEATURE:
<223> OTHER INFORMATION: E. coli pelB +Brazzein(R32H) gene

<400> SEQUENCE: 64

```
atgaaatacc tgctgccgac cgctgctgct ggtctgctgc tcctcgctgc ccagccggcg      60
atggccgata agtgcaagaa ggtttacgaa aattacccag tttctaagtg ccaacttgct     120
aatcaatgca attacgattg caagcttgat aagcatgctc actctggaga atgcttttac     180
gatgaaaaga gaaatcttca atgcatttgc gattactgcg aatactaa                 228
```

<210> SEQ ID NO 65
<211> LENGTH: 228
<212> TYPE: DNA
<213> ORGANISM: Artificial Sequence
<220> FEATURE:
<223> OTHER INFORMATION: E. coli pelB +Brazzein(R32D) gene

<400> SEQUENCE: 65

```
atgaaatacc tgctgccgac cgctgctgct ggtctgctgc tcctcgctgc ccagccggcg      60
atggccgata agtgcaagaa ggtttacgaa aattacccag tttctaagtg ccaacttgct     120
aatcaatgca attacgattg caagcttgat aagcatgctg actctggaga atgcttttac     180
gatgaaaaga gaaatcttca atgcatttgc gattactgcg aatactaa                 228
```

<210> SEQ ID NO 66
<211> LENGTH: 228
<212> TYPE: DNA
<213> ORGANISM: Artificial Sequence
<220> FEATURE:
<223> OTHER INFORMATION: E. coli pelB +Brazzein(R32E) gene

<400> SEQUENCE: 66

```
atgaaatacc tgctgccgac cgctgctgct ggtctgctgc tcctcgctgc ccagccggcg      60
atggccgata agtgcaagaa ggtttacgaa aattacccag tttctaagtg ccaacttgct     120
aatcaatgca attacgattg caagcttgat aagcatgctg aatctggaga atgcttttac     180
gatgaaaaga gaaatcttca atgcatttgc gattactgcg aatactaa                 228
```

<210> SEQ ID NO 67
<211> LENGTH: 228
<212> TYPE: DNA
<213> ORGANISM: Artificial Sequence
<220> FEATURE:
<223> OTHER INFORMATION: E. coli pelB +Brazzein(E35A) gene

```
<400> SEQUENCE: 67
atgaaatacc tgctgccgac cgctgctgct ggtctgctgc tcctcgctgc ccagccggcg     60
atggccgata agtgcaagaa ggtttacgaa aattacccag tttctaagtg ccaacttgct    120
aatcaatgca attacgattg caagcttgat aagcatgctg aatctggagc ttgcttttac    180
gatgaaaaga gaaatcttca atgcatttgc gattactgcg aatactaa                228

<210> SEQ ID NO 68
<211> LENGTH: 229
<212> TYPE: DNA
<213> ORGANISM: Artificial Sequence
<220> FEATURE:
<223> OTHER INFORMATION: E. coli pelB +Brazzein(E35D) gene

<400> SEQUENCE: 68
atgaaatacc tgctgccgac cgctgctgct ggtctgctgc tcctcgctgc ccagccggcg     60
atggccgata agtgcaagaa ggtttacgaa aattacccag tttctaagtg ccaacttgct    120
aatcaatgca attacgattg caagcttgat aagcgtgcta gatctggaga ctgcttttac    180
gatgaataag agaaatcttc aatgcatttg cgattactgc gaatactaa                229

<210> SEQ ID NO 69
<211> LENGTH: 228
<212> TYPE: DNA
<213> ORGANISM: Artificial Sequence
<220> FEATURE:
<223> OTHER INFORMATION: E. coli pelB +Brazzein(E35K) gene

<400> SEQUENCE: 69
atgaaatacc tgctgccgac cgctgctgct ggtctgctgc tcctcgctgc ccagccggcg     60
atggccgata agtgcaagaa ggtttacgaa aattacccag tttctaagtg ccaacttgct    120
aatcaatgca attacgattg caagcttaaa aagcatgctg aatctggaaa atgcttttac    180
gatgaaaaga gaaatcttca atgcatttgc gattactgcg aatactaa                228

<210> SEQ ID NO 70
<211> LENGTH: 228
<212> TYPE: DNA
<213> ORGANISM: Artificial Sequence
<220> FEATURE:
<223> OTHER INFORMATION: E. coli pelB +Brazzein(E35H) gene

<400> SEQUENCE: 70
atgaaatacc tgctgccgac cgctgctgct ggtctgctgc tcctcgctgc ccagccggcg     60
atggccgata agtgcaagaa ggtttacgaa aattacccag tttctaagtg ccaacttgct    120
aatcaatgca attacgattg caagcttcac aagcatgctc actctggaca ctgcttttac    180
gatgaaaaga gaaatcttca atgcatttgc gattactgcg aatactaa                228

<210> SEQ ID NO 71
<211> LENGTH: 228
<212> TYPE: DNA
<213> ORGANISM: Artificial Sequence
<220> FEATURE:
<223> OTHER INFORMATION: E. coli pelB +Brazzein(E35R) gene

<400> SEQUENCE: 71
atgaaatacc tgctgccgac cgctgctgct ggtctgctgc tcctcgctgc ccagccggcg     60
atggccgata agtgcaagaa ggtttacgaa aattacccag tttctaagtg ccaacttgct    120
aatcaatgca attacgattg caagcttcgt aagcatgctc actctggaca ctgcttttac    180
```
gatgaaaaga gaaatcttca atgcatttgc gattactgcg aatactaa          228

<210> SEQ ID NO 72
<211> LENGTH: 228
<212> TYPE: DNA
<213> ORGANISM: Artificial Sequence
<220> FEATURE:
<223> OTHER INFORMATION: E. coli pelB +Brazzein(E40A) gene

<400> SEQUENCE: 72
atgaaatacc tgctgccgac cgctgctgct ggtctgctgc tcctcgctgc ccagccggcg     60
atggccgata agtgcaagaa ggtttacgaa aattacccag tttctaagtg ccaacttgct    120
aatcaatgca attacgattg caagcttgat aagcatgctc actctggaca ctgcttttac    180
gatgctaaga gaaatcttca atgcatttgc gattactgcg aatactaa                 228

<210> SEQ ID NO 73
<211> LENGTH: 228
<212> TYPE: DNA
<213> ORGANISM: Artificial Sequence
<220> FEATURE:
<223> OTHER INFORMATION: E. coli pelB +Brazzein(E40D) gene

<400> SEQUENCE: 73
atgaaatacc tgctgccgac cgctgctgct ggtctgctgc tcctcgctgc ccagccggcg     60
atggccgata agtgcaagaa ggtttacgaa aattacccag tttctaagtg ccaacttgct    120
aatcaatgca attacgattg caagcttgat aagcatgctc actctggaca ctgcttttac    180
gatgacaaga gaaatcttca atgcatttgc gattactgcg aatactaa                 228

<210> SEQ ID NO 74
<211> LENGTH: 228
<212> TYPE: DNA
<213> ORGANISM: Artificial Sequence
<220> FEATURE:
<223> OTHER INFORMATION: E. coli pelB +Brazzein(E40K) gene

<400> SEQUENCE: 74
atgaaatacc tgctgccgac cgctgctgct ggtctgctgc tcctcgctgc ccagccggcg     60
atggccgata agtgcaagaa ggtttacgaa aattacccag tttctaagtg ccaacttgct    120
aatcaatgca attacgattg caagcttgat aagcatgctc actctggaca ctgcttttac    180
gataaaaaga gaaatcttca atgcatttgc gattactgcg aatactaa                 228

<210> SEQ ID NO 75
<211> LENGTH: 228
<212> TYPE: DNA
<213> ORGANISM: Artificial Sequence
<220> FEATURE:
<223> OTHER INFORMATION: E. coli pelB +Brazzein(E40H) gene

<400> SEQUENCE: 75
atgaaatacc tgctgccgac cgctgctgct ggtctgctgc tcctcgctgc ccagccggcg     60
atggccgata agtgcaagaa ggtttacgaa aattacccag tttctaagtg ccaacttgct    120
aatcaatgca attacgattg caagcttgat aagcatgctc actctggaca ctgcttttac    180
gatcacaaga gaaatcttca atgcatttgc gattactgcg aatactaa                 228

<210> SEQ ID NO 76
<211> LENGTH: 228
<212> TYPE: DNA
<213> ORGANISM: Artificial Sequence
<220> FEATURE:

-continued

<223> OTHER INFORMATION: E. coli pelB +Brazzein(E40R) gene

<400> SEQUENCE: 76

| atgaaatacc tgctgccgac cgctgctgct ggtctgctgc tcctcgctgc ccagccggcg | 60 |
| atggccgata agtgcaagaa ggtttacgaa aattacccag tttctaagtg ccaacttgct | 120 |
| aatcaatgca attacgattg caagcttgat aagcatgctc actctggaca ctgcttttac | 180 |
| gatcgtaaga gaaatcttca atgcatttgc gattactgcg aatactaa | 228 |

<210> SEQ ID NO 77
<211> LENGTH: 228
<212> TYPE: DNA
<213> ORGANISM: Artificial Sequence
<220> FEATURE:
<223> OTHER INFORMATION: E. coli pelB +Brazzein(R42A) gene

<400> SEQUENCE: 77

| atgaaatacc tgctgccgac cgctgctgct ggtctgctgc tcctcgctgc ccagccggcg | 60 |
| atggccgata agtgcaagaa ggtttacgaa aattacccag tttctaagtg ccaacttgct | 120 |
| aatcaatgca attacgattg caagcttgat aagcatgcta gatctggaga atgcttttac | 180 |
| gatgaaaagg ctaatcttca atgcatttgc gattactgcg aatactaa | 228 |

<210> SEQ ID NO 78
<211> LENGTH: 228
<212> TYPE: DNA
<213> ORGANISM: Artificial Sequence
<220> FEATURE:
<223> OTHER INFORMATION: E. coli pelB +Brazzein(R42K) gene

<400> SEQUENCE: 78

| atgaaatacc tgctgccgac cgctgctgct ggtctgctgc tcctcgctgc ccagccggcg | 60 |
| atggccgata agtgcaagaa ggtttacgaa aattacccag tttctaagtg ccaacttgct | 120 |
| aatcaatgca attacgattg caagcttgat aagcatgcta gatctggaga atgcttttac | 180 |
| gatgaaaaga aaaatcttca atgcatttgc gattactgcg aatactaa | 228 |

<210> SEQ ID NO 79
<211> LENGTH: 228
<212> TYPE: DNA
<213> ORGANISM: Artificial Sequence
<220> FEATURE:
<223> OTHER INFORMATION: E. coli pelB +Brazzein(R42H) gene

<400> SEQUENCE: 79

| atgaaatacc tgctgccgac cgctgctgct ggtctgctgc tcctcgctgc ccagccggcg | 60 |
| atggccgata agtgcaagaa ggtttacgaa aattacccag tttctaagtg ccaacttgct | 120 |
| aatcaatgca attacgattg caagcttgat aagcatgcta gatctggaga atgcttttac | 180 |
| gatgaaaagc acaatcttca atgcatttgc gattactgcg aatactaa | 228 |

<210> SEQ ID NO 80
<211> LENGTH: 228
<212> TYPE: DNA
<213> ORGANISM: Artificial Sequence
<220> FEATURE:
<223> OTHER INFORMATION: E. coli pelB +Brazzein(R42D) gene

<400> SEQUENCE: 80

| atgaaatacc tgctgccgac cgctgctgct ggtctgctgc tcctcgctgc ccagccggcg | 60 |
| atggccgata agtgcaagaa ggtttacgaa aattacccag tttctaagtg ccaacttgct | 120 |

```
aatcaatgca attacgattg caagcttgat aagcatgcta gatctggaga atgctttttac      180 gatgaaaagg acaatcttca atgcatttgc gattactgcg aatactaa                    228

<210> SEQ ID NO 81
<211> LENGTH: 228
<212> TYPE: DNA
<213> ORGANISM: Artificial Sequence
<220> FEATURE:
<223> OTHER INFORMATION: E. coli pelB +Brazzein(R42E) gene

<400> SEQUENCE: 81
atgaaatacc tgctgccgac cgctgctgct ggtctgctgc tcctcgctgc ccagccggcg       60
atggccgata agtgcaagaa ggtttacgaa aattacccag tttctaagtg ccaacttgct      120
aatcaatgca attacgattg caagcttgat aagcatgcta gatctggaga atgcttttac      180
gatgaaaagg aaaatcttca atgcatttgc gattactgcg aatactaa                    228

<210> SEQ ID NO 82
<211> LENGTH: 53
<212> TYPE: PRT
<213> ORGANISM: Artificial Sequence
<220> FEATURE:
<223> OTHER INFORMATION: Brazzein(minor type)

<400> SEQUENCE: 82

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
            20                  25                  30

Ser Gly Glu Cys Phe Tyr Asp Glu Lys Arg Asn Leu Gln Cys Ile Cys
        35                  40                  45

Asp Tyr Cys Glu Tyr
    50

<210> SEQ ID NO 83
<211> LENGTH: 53
<212> TYPE: PRT
<213> ORGANISM: Artificial Sequence
<220> FEATURE:
<223> OTHER INFORMATION: Brazzein(K5A)

<400> SEQUENCE: 83

Asp Lys Cys Lys Ala Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
            20                  25                  30

Ser Gly Glu Cys Phe Tyr Asp Glu Lys Arg Asn Leu Gln Cys Ile Cys
        35                  40                  45

Asp Tyr Cys Glu Tyr
    50

<210> SEQ ID NO 84
<211> LENGTH: 53
<212> TYPE: PRT
<213> ORGANISM: Artificial Sequence
<220> FEATURE:
<223> OTHER INFORMATION: Brazzein(K5D)

<400> SEQUENCE: 84

Asp Lys Cys Lys Asp Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
```

```
                    20                  25                  30

Ser Gly Glu Cys Phe Tyr Asp Glu Lys Arg Asn Leu Gln Cys Ile Cys
        35                  40                  45

Asp Tyr Cys Glu Tyr
        50

<210> SEQ ID NO 85
<211> LENGTH: 53
<212> TYPE: PRT
<213> ORGANISM: Artificial Sequence
<220> FEATURE:
<223> OTHER INFORMATION: Brazzein(K5E)

<400> SEQUENCE: 85

Asp Lys Cys Lys Glu Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
                20                  25                  30

Ser Gly Glu Cys Phe Tyr Asp Glu Lys Arg Asn Leu Gln Cys Ile Cys
        35                  40                  45

Asp Tyr Cys Glu Tyr
        50

<210> SEQ ID NO 86
<211> LENGTH: 53
<212> TYPE: PRT
<213> ORGANISM: Artificial Sequence
<220> FEATURE:
<223> OTHER INFORMATION: Brazzein(K5H)

<400> SEQUENCE: 86

Asp Lys Cys Lys His Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
                20                  25                  30

Ser Gly Glu Cys Phe Tyr Asp Glu Lys Arg Asn Leu Gln Cys Ile Cys
        35                  40                  45

Asp Tyr Cys Glu Tyr
        50

<210> SEQ ID NO 87
<211> LENGTH: 53
<212> TYPE: PRT
<213> ORGANISM: Artificial Sequence
<220> FEATURE:
<223> OTHER INFORMATION: Brazzein(K5R)

<400> SEQUENCE: 87

Asp Lys Cys Lys Arg Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
                20                  25                  30

Ser Gly Glu Cys Phe Tyr Asp Glu Lys Arg Asn Leu Gln Cys Ile Cys
        35                  40                  45

Asp Tyr Cys Glu Tyr
        50

<210> SEQ ID NO 88
<211> LENGTH: 53
<212> TYPE: PRT
<213> ORGANISM: Artificial Sequence
<220> FEATURE:
```

<223> OTHER INFORMATION: Brazzein(D28A)

<400> SEQUENCE: 88

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Ala Lys His Ala Arg
            20                  25                  30

Ser Gly Glu Cys Phe Tyr Asp Glu Lys Arg Asn Leu Gln Cys Ile Cys
        35                  40                  45

Asp Tyr Cys Glu Tyr
    50

<210> SEQ ID NO 89
<211> LENGTH: 53
<212> TYPE: PRT
<213> ORGANISM: Artificial Sequence
<220> FEATURE:
<223> OTHER INFORMATION: Brazzein(D28H)

<400> SEQUENCE: 89

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu His Lys His Ala Arg
            20                  25                  30

Ser Gly Glu Cys Phe Tyr Asp Glu Lys Arg Asn Leu Gln Cys Ile Cys
        35                  40                  45

Asp Tyr Cys Glu Tyr
    50

<210> SEQ ID NO 90
<211> LENGTH: 53
<212> TYPE: PRT
<213> ORGANISM: Artificial Sequence
<220> FEATURE:
<223> OTHER INFORMATION: Brazzein(D28K)

<400> SEQUENCE: 90

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Lys Lys His Ala Arg
            20                  25                  30

Ser Gly Glu Cys Phe Tyr Asp Glu Lys Arg Asn Leu Gln Cys Ile Cys
        35                  40                  45

Asp Tyr Cys Glu Tyr
    50

<210> SEQ ID NO 91
<211> LENGTH: 53
<212> TYPE: PRT
<213> ORGANISM: Artificial Sequence
<220> FEATURE:
<223> OTHER INFORMATION: Brazzein(D28R)

<400> SEQUENCE: 91

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
            20                  25                  30

Ser Gly Glu Cys Phe Tyr Asp Glu Lys Arg Asn Leu Gln Cys Ile Cys
        35                  40                  45

Asp Tyr Cys Glu Tyr

<210> SEQ ID NO 92
<211> LENGTH: 53
<212> TYPE: PRT
<213> ORGANISM: Artificial Sequence
<220> FEATURE:
<223> OTHER INFORMATION: Brazzein(D28E)

<400> SEQUENCE: 92

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Glu Lys His Ala Arg
            20                  25                  30

Ser Gly Glu Cys Phe Tyr Asp Glu Lys Arg Asn Leu Gln Cys Ile Cys
        35                  40                  45

Asp Tyr Cys Glu Tyr
        50

<210> SEQ ID NO 93
<211> LENGTH: 53
<212> TYPE: PRT
<213> ORGANISM: Artificial Sequence
<220> FEATURE:
<223> OTHER INFORMATION: Brazzein(K29A)

<400> SEQUENCE: 93

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Ala His Ala Arg
            20                  25                  30

Ser Gly Glu Cys Phe Tyr Asp Glu Lys Arg Asn Leu Gln Cys Ile Cys
        35                  40                  45

Asp Tyr Cys Glu Tyr
        50

<210> SEQ ID NO 94
<211> LENGTH: 53
<212> TYPE: PRT
<213> ORGANISM: Artificial Sequence
<220> FEATURE:
<223> OTHER INFORMATION: Brazzein(K29R)

<400> SEQUENCE: 94

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Arg His Ala Arg
            20                  25                  30

Ser Gly Glu Cys Phe Tyr Asp Glu Lys Arg Asn Leu Gln Cys Ile Cys
        35                  40                  45

Asp Tyr Cys Glu Tyr
        50

<210> SEQ ID NO 95
<211> LENGTH: 53
<212> TYPE: PRT
<213> ORGANISM: Artificial Sequence
<220> FEATURE:
<223> OTHER INFORMATION: Brazzein(K29H)

<400> SEQUENCE: 95

Asp Lys Cys Lys Lys Val Tyr Glu Asn Tyr Pro Val Ser Lys Cys Gln
1               5                   10                  15

-continued

Leu Ala Asn Gln Cys Asn Tyr Asp Cys Lys Leu Arg His His Ala Arg
           20                  25                  30

Ser Gly Glu Cys Phe Tyr Asp Glu Lys Arg Asn Leu Gln Cys Ile Cys
           35                  40                  45

Asp Tyr Cys Glu Tyr
        50

<210> SEQ ID NO 96
<211> LENGTH: 53
<212> TYPE: PRT
<213> ORGANISM: Artificial Sequence
<220> FEATURE:
<223> OTHER INFORMATION: Brazzein(K29D)

<400> SEQUENCE: 96

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Asp His Ala Arg
           20                  25                  30

Ser Gly Glu Cys Phe Tyr Asp Glu Lys Arg Asn Leu Gln Cys Ile Cys
           35                  40                  45

Asp Tyr Cys Glu Tyr
        50

<210> SEQ ID NO 97
<211> LENGTH: 53
<212> TYPE: PRT
<213> ORGANISM: Artificial Sequence
<220> FEATURE:
<223> OTHER INFORMATION: Brazzein(K29E)

<400> SEQUENCE: 97

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Glu His Ala Arg
           20                  25                  30

Ser Gly Glu Cys Phe Tyr Asp Glu Lys Arg Asn Leu Gln Cys Ile Cys
           35                  40                  45

Asp Tyr Cys Glu Tyr
        50

<210> SEQ ID NO 98
<211> LENGTH: 53
<212> TYPE: PRT
<213> ORGANISM: Artificial Sequence
<220> FEATURE:
<223> OTHER INFORMATION: Brazzein(H30A)

<400> SEQUENCE: 98

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys Ala Ala Arg
           20                  25                  30

Ser Gly Glu Cys Phe Tyr Asp Glu Lys Arg Asn Leu Gln Cys Ile Cys
           35                  40                  45

Asp Tyr Cys Glu Tyr
        50

<210> SEQ ID NO 99
<211> LENGTH: 53
<212> TYPE: PRT

```
<213> ORGANISM: Artificial Sequence
<220> FEATURE:
<223> OTHER INFORMATION: Brazzein(H30K)

<400> SEQUENCE: 99

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys Lys Ala Arg
            20                  25                  30

Ser Gly Glu Cys Phe Tyr Asp Glu Lys Arg Asn Leu Gln Cys Ile Cys
        35                  40                  45

Asp Tyr Cys Glu Tyr
    50

<210> SEQ ID NO 100
<211> LENGTH: 53
<212> TYPE: PRT
<213> ORGANISM: Artificial Sequence
<220> FEATURE:
<223> OTHER INFORMATION: Brazzein(H30R)

<400> SEQUENCE: 100

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys Arg Ala Arg
            20                  25                  30

Ser Gly Glu Cys Phe Tyr Asp Glu Lys Arg Asn Leu Gln Cys Ile Cys
        35                  40                  45

Asp Tyr Cys Glu Tyr
    50

<210> SEQ ID NO 101
<211> LENGTH: 53
<212> TYPE: PRT
<213> ORGANISM: Artificial Sequence
<220> FEATURE:
<223> OTHER INFORMATION: Brazzein(H30D)

<400> SEQUENCE: 101

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys Asp Ala Arg
            20                  25                  30

Ser Gly Glu Cys Phe Tyr Asp Glu Lys Arg Asn Leu Gln Cys Ile Cys
        35                  40                  45

Asp Tyr Cys Glu Tyr
    50

<210> SEQ ID NO 102
<211> LENGTH: 53
<212> TYPE: PRT
<213> ORGANISM: Artificial Sequence
<220> FEATURE:
<223> OTHER INFORMATION: Brazzein(H30E)

<400> SEQUENCE: 102

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys Glu Ala Arg
            20                  25                  30

Ser Gly Glu Cys Phe Tyr Asp Glu Lys Arg Asn Leu Gln Cys Ile Cys
        35                  40                  45
```

Asp Tyr Cys Glu Tyr
    50

<210> SEQ ID NO 103
<211> LENGTH: 53
<212> TYPE: PRT
<213> ORGANISM: Artificial Sequence
<220> FEATURE:
<223> OTHER INFORMATION: Brazzein(R32A)

<400> SEQUENCE: 103

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Ala
            20                  25                  30

Ser Gly Glu Cys Phe Tyr Asp Glu Lys Arg Asn Leu Gln Cys Ile Cys
        35                  40                  45

Asp Tyr Cys Glu Tyr
    50

<210> SEQ ID NO 104
<211> LENGTH: 53
<212> TYPE: PRT
<213> ORGANISM: Artificial Sequence
<220> FEATURE:
<223> OTHER INFORMATION: Brazzein(R32K)

<400> SEQUENCE: 104

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Lys
            20                  25                  30

Ser Gly Glu Cys Phe Tyr Asp Glu Lys Arg Asn Leu Gln Cys Ile Cys
        35                  40                  45

Asp Tyr Cys Glu Tyr
    50

<210> SEQ ID NO 105
<211> LENGTH: 53
<212> TYPE: PRT
<213> ORGANISM: Artificial Sequence
<220> FEATURE:
<223> OTHER INFORMATION: Brazzein(R32H)

<400> SEQUENCE: 105

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala His
            20                  25                  30

Ser Gly Glu Cys Phe Tyr Asp Glu Lys Arg Asn Leu Gln Cys Ile Cys
        35                  40                  45

Asp Tyr Cys Glu Tyr
    50

<210> SEQ ID NO 106
<211> LENGTH: 53
<212> TYPE: PRT
<213> ORGANISM: Artificial Sequence
<220> FEATURE:
<223> OTHER INFORMATION: Brazzein(R32D)

<400> SEQUENCE: 106

```
Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Asp
            20                  25                  30

Ser Gly Glu Cys Phe Tyr Asp Glu Lys Arg Asn Leu Gln Cys Ile Cys
        35                  40                  45

Asp Tyr Cys Glu Tyr
    50

<210> SEQ ID NO 107
<211> LENGTH: 53
<212> TYPE: PRT
<213> ORGANISM: Artificial Sequence
<220> FEATURE:
<223> OTHER INFORMATION: Brazzein(R32E)

<400> SEQUENCE: 107

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Glu
            20                  25                  30

Ser Gly Glu Cys Phe Tyr Asp Glu Lys Arg Asn Leu Gln Cys Ile Cys
        35                  40                  45

Asp Tyr Cys Glu Tyr
    50

<210> SEQ ID NO 108
<211> LENGTH: 53
<212> TYPE: PRT
<213> ORGANISM: Artificial Sequence
<220> FEATURE:
<223> OTHER INFORMATION: Brazzein(E35A)

<400> SEQUENCE: 108

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
            20                  25                  30

Ser Gly Ala Cys Phe Tyr Asp Glu Lys Arg Asn Leu Gln Cys Ile Cys
        35                  40                  45

Asp Tyr Cys Glu Tyr
    50

<210> SEQ ID NO 109
<211> LENGTH: 53
<212> TYPE: PRT
<213> ORGANISM: Artificial Sequence
<220> FEATURE:
<223> OTHER INFORMATION: Brazzein(E35D)

<400> SEQUENCE: 109

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
            20                  25                  30

Ser Gly Asp Cys Phe Tyr Asp Glu Lys Arg Asn Leu Gln Cys Ile Cys
        35                  40                  45

Asp Tyr Cys Glu Tyr
    50

<210> SEQ ID NO 110
```

```
<211> LENGTH: 53
<212> TYPE: PRT
<213> ORGANISM: Artificial Sequence
<220> FEATURE:
<223> OTHER INFORMATION: Brazzein(E35K)

<400> SEQUENCE: 110

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
            20                  25                  30

Ser Gly Lys Cys Phe Tyr Asp Glu Lys Arg Asn Leu Gln Cys Ile Cys
        35                  40                  45

Asp Tyr Cys Glu Tyr
    50

<210> SEQ ID NO 111
<211> LENGTH: 53
<212> TYPE: PRT
<213> ORGANISM: Artificial Sequence
<220> FEATURE:
<223> OTHER INFORMATION: Brazzein(E35H)

<400> SEQUENCE: 111

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
            20                  25                  30

Ser Gly His Cys Phe Tyr Asp Glu Lys Arg Asn Leu Gln Cys Ile Cys
        35                  40                  45

Asp Tyr Cys Glu Tyr
    50

<210> SEQ ID NO 112
<211> LENGTH: 53
<212> TYPE: PRT
<213> ORGANISM: Artificial Sequence
<220> FEATURE:
<223> OTHER INFORMATION: Brazzein(E35R)

<400> SEQUENCE: 112

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
            20                  25                  30

Ser Gly Arg Cys Phe Tyr Asp Glu Lys Arg Asn Leu Gln Cys Ile Cys
        35                  40                  45

Asp Tyr Cys Glu Tyr
    50

<210> SEQ ID NO 113
<211> LENGTH: 53
<212> TYPE: PRT
<213> ORGANISM: Artificial Sequence
<220> FEATURE:
<223> OTHER INFORMATION: Brazzein(E40A)

<400> SEQUENCE: 113

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
            20                  25                  30
```

-continued

Ser Gly Glu Cys Phe Tyr Asp Ala Lys Arg Asn Leu Gln Cys Ile Cys
        35                  40                  45

Asp Tyr Cys Glu Tyr
    50

<210> SEQ ID NO 114
<211> LENGTH: 53
<212> TYPE: PRT
<213> ORGANISM: Artificial Sequence
<220> FEATURE:
<223> OTHER INFORMATION: Brazzein(E40D)

<400> SEQUENCE: 114

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
            20                  25                  30

Ser Gly Glu Cys Phe Tyr Asp Asp Lys Arg Asn Leu Gln Cys Ile Cys
        35                  40                  45

Asp Tyr Cys Glu Tyr
    50

<210> SEQ ID NO 115
<211> LENGTH: 53
<212> TYPE: PRT
<213> ORGANISM: Artificial Sequence
<220> FEATURE:
<223> OTHER INFORMATION: Brazzein(E40K)

<400> SEQUENCE: 115

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
            20                  25                  30

Ser Gly Glu Cys Phe Tyr Asp Lys Lys Arg Asn Leu Gln Cys Ile Cys
        35                  40                  45

Asp Tyr Cys Glu Tyr
    50

<210> SEQ ID NO 116
<211> LENGTH: 53
<212> TYPE: PRT
<213> ORGANISM: Artificial Sequence
<220> FEATURE:
<223> OTHER INFORMATION: Brazzein(E40H)

<400> SEQUENCE: 116

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
            20                  25                  30

Ser Gly Glu Cys Phe Tyr Asp His Lys Arg Asn Leu Gln Cys Ile Cys
        35                  40                  45

Asp Tyr Cys Glu Tyr
    50

<210> SEQ ID NO 117
<211> LENGTH: 53
<212> TYPE: PRT
<213> ORGANISM: Artificial Sequence
<220> FEATURE:
<223> OTHER INFORMATION: Brazzein(E40R)

<400> SEQUENCE: 117

```
Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
            20                  25                  30

Ser Gly Glu Cys Phe Tyr Asp Arg Lys Arg Asn Leu Gln Cys Ile Cys
        35                  40                  45

Asp Tyr Cys Glu Tyr
        50
```

<210> SEQ ID NO 118
<211> LENGTH: 53
<212> TYPE: PRT
<213> ORGANISM: Artificial Sequence
<220> FEATURE:
<223> OTHER INFORMATION: Brazzein(R42A)

<400> SEQUENCE: 118

```
Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
            20                  25                  30

Ser Gly Glu Cys Phe Tyr Asp Glu Lys Ala Asn Leu Gln Cys Ile Cys
        35                  40                  45

Asp Tyr Cys Glu Tyr
        50
```

<210> SEQ ID NO 119
<211> LENGTH: 53
<212> TYPE: PRT
<213> ORGANISM: Artificial Sequence
<220> FEATURE:
<223> OTHER INFORMATION: Brazzein(R42K)

<400> SEQUENCE: 119

```
Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
            20                  25                  30

Ser Gly Glu Cys Phe Tyr Asp Glu Lys Lys Asn Leu Gln Cys Ile Cys
        35                  40                  45

Asp Tyr Cys Glu Tyr
        50
```

<210> SEQ ID NO 120
<211> LENGTH: 53
<212> TYPE: PRT
<213> ORGANISM: Artificial Sequence
<220> FEATURE:
<223> OTHER INFORMATION: Brazzein(R42H)

<400> SEQUENCE: 120

```
Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
            20                  25                  30

Ser Gly Glu Cys Phe Tyr Asp Glu Lys His Asn Leu Gln Cys Ile Cys
        35                  40                  45

Asp Tyr Cys Glu Tyr
        50
```

```
<210> SEQ ID NO 121
<211> LENGTH: 53
<212> TYPE: PRT
<213> ORGANISM: Artificial Sequence
<220> FEATURE:
<223> OTHER INFORMATION: Brazzein(R42D)

<400> SEQUENCE: 121

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
            20                  25                  30

Ser Gly Glu Cys Phe Tyr Asp Glu Lys Asp Asn Leu Gln Cys Ile Cys
        35                  40                  45

Asp Tyr Cys Glu Tyr
    50

<210> SEQ ID NO 122
<211> LENGTH: 53
<212> TYPE: PRT
<213> ORGANISM: Artificial Sequence
<220> FEATURE:
<223> OTHER INFORMATION: Brazzein(R42E)

<400> SEQUENCE: 122

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Arg
            20                  25                  30

Ser Gly Glu Cys Phe Tyr Asp Glu Lys Glu Asn Leu Gln Cys Ile Cys
        35                  40                  45

Asp Tyr Cys Glu Tyr
    50

<210> SEQ ID NO 123
<211> LENGTH: 228
<212> TYPE: DNA
<213> ORGANISM: Artificial Sequence
<220> FEATURE:
<223> OTHER INFORMATION: E. coli pelB +Brazzein(H30R_E35D) gene

<400> SEQUENCE: 123
atgaaatacc tgctgccgac cgctgctgct ggtctgctgc tcctcgctgc ccagccggcg      60
atggccgata agtgcaagaa ggtttacgaa aattacccag tttctaagtg ccaacttgct     120
aatcaatgca attacgattg caagcttgat aagcgtgcta gatctggaga ctgcttttac     180
gatgaaaaga gaaatcttca atgcatttgc gattactgcg aatactaa                  228

<210> SEQ ID NO 124
<211> LENGTH: 228
<212> TYPE: DNA
<213> ORGANISM: Artificial Sequence
<220> FEATURE:
<223> OTHER INFORMATION: E. coli pelB +Brazzein(H30R_E40A) gene

<400> SEQUENCE: 124
atgaaatacc tgctgccgac cgctgctgct ggtctgctgc tcctcgctgc ccagccggcg      60
atggccgata agtgcaagaa ggtttacgaa aattacccag tttctaagtg ccaacttgct     120
aatcaatgca attacgattg caagcttgat aagcgtgcta gatctggaga atgcttttac     180
gatgctaaga gaaatcttca atgcatttgc gattactgcg aatactaa                  228
```

<210> SEQ ID NO 125
<211> LENGTH: 228
<212> TYPE: DNA
<213> ORGANISM: Artificial Sequence
<220> FEATURE:
<223> OTHER INFORMATION: E. coli pelB +Brazzein(H30R_E40D) gene

<400> SEQUENCE: 125

```
atgaaatacc tgctgccgac cgctgctgct ggtctgctgc tcctcgctgc ccagccggcg    60
atggccgata agtgcaagaa ggtttacgaa aattacccag tttctaagtg ccaacttgct   120
aatcaatgca attacgattg caagcttgat aagcgtgcta gatctggaga atgcttttac   180
gatgacaaga gaaatcttca atgcatttgc gattactgcg aatactaa                228
```

<210> SEQ ID NO 126
<211> LENGTH: 228
<212> TYPE: DNA
<213> ORGANISM: Artificial Sequence
<220> FEATURE:
<223> OTHER INFORMATION: E. coli pelB +Brazzein(H30R_E40K) gene

<400> SEQUENCE: 126

```
atgaaatacc tgctgccgac cgctgctgct ggtctgctgc tcctcgctgc ccagccggcg    60
atggccgata agtgcaagaa ggtttacgaa aattacccag tttctaagtg ccaacttgct   120
aatcaatgca attacgattg caagcttgat aagcgtgcta gatctggaga atgcttttac   180
gataaaaaga gaaatcttca atgcatttgc gattactgcg aatactaa                228
```

<210> SEQ ID NO 127
<211> LENGTH: 228
<212> TYPE: DNA
<213> ORGANISM: Artificial Sequence
<220> FEATURE:
<223> OTHER INFORMATION: E. coli pelB +Brazzein(H30R_E40R) gene

<400> SEQUENCE: 127

```
atgaaatacc tgctgccgac cgctgctgct ggtctgctgc tcctcgctgc ccagccggcg    60
atggccgata agtgcaagaa ggtttacgaa aattacccag tttctaagtg ccaacttgct   120
aatcaatgca attacgattg caagcttgat aagcgtgcta gatctggaga atgcttttac   180
gatcgtaaga gaaatcttca atgcatttgc gattactgcg aatactaa                228
```

<210> SEQ ID NO 128
<211> LENGTH: 228
<212> TYPE: DNA
<213> ORGANISM: Artificial Sequence
<220> FEATURE:
<223> OTHER INFORMATION: E. coli pelB +Brazzein(E35D_E40A) gene

<400> SEQUENCE: 128

```
atgaaatacc tgctgccgac cgctgctgct ggtctgctgc tcctcgctgc ccagccggcg    60
atggccgata agtgcaagaa ggtttacgaa aattacccag tttctaagtg ccaacttgct   120
aatcaatgca attacgattg caagcttcgt aagcatgctc actctggaca ctgcttttac   180
gatgctaaga gaaatcttca atgcatttgc gattactgcg aatactaa                228
```

<210> SEQ ID NO 129
<211> LENGTH: 228
<212> TYPE: DNA
<213> ORGANISM: Artificial Sequence
<220> FEATURE:
<223> OTHER INFORMATION: E. coli pelB +Brazzein(E35D_E40D) gene

<400> SEQUENCE: 129

```
atgaaatacc tgctgccgac cgctgctgct ggtctgctgc tcctcgctgc ccagccggcg      60
atggccgata agtgcaagaa ggtttacgaa aattacccag tttctaagtg ccaacttgct     120
aatcaatgca attacgattg caagcttcgt aagcatgctc actctggaca ctgcttttac     180
gatgacaaga gaaatcttca atgcatttgc gattactgcg aatactaa                  228
```

<210> SEQ ID NO 130
<211> LENGTH: 228
<212> TYPE: DNA
<213> ORGANISM: Artificial Sequence
<220> FEATURE:
<223> OTHER INFORMATION: E. coli pelB +Brazzein(E35D_E40K) gene

<400> SEQUENCE: 130

```
atgaaatacc tgctgccgac cgctgctgct ggtctgctgc tcctcgctgc ccagccggcg      60
atggccgata agtgcaagaa ggtttacgaa aattacccag tttctaagtg ccaacttgct     120
aatcaatgca attacgattg caagcttcgt aagcatgctc actctggaca ctgcttttac     180
gataaaaaga gaaatcttca atgcatttgc gattactgcg aatactaa                  228
```

<210> SEQ ID NO 131
<211> LENGTH: 228
<212> TYPE: DNA
<213> ORGANISM: Artificial Sequence
<220> FEATURE:
<223> OTHER INFORMATION: E. coli pelB +Brazzein(E35D_E40R) gene

<400> SEQUENCE: 131

```
atgaaatacc tgctgccgac cgctgctgct ggtctgctgc tcctcgctgc ccagccggcg      60
atggccgata agtgcaagaa ggtttacgaa aattacccag tttctaagtg ccaacttgct     120
aatcaatgca attacgattg caagcttcgt aagcatgctc actctggaca ctgcttttac     180
gatcgtaaga gaaatcttca atgcatttgc gattactgcg aatactaa                  228
```

<210> SEQ ID NO 132
<211> LENGTH: 228
<212> TYPE: DNA
<213> ORGANISM: Artificial Sequence
<220> FEATURE:
<223> OTHER INFORMATION: E. coli pelB +Brazzein(H30R_E35D_E40A) gene

<400> SEQUENCE: 132

```
atgaaatacc tgctgccgac cgctgctgct ggtctgctgc tcctcgctgc ccagccggcg      60
atggccgata agtgcaagaa ggtttacgaa aattacccag tttctaagtg ccaacttgct     120
aatcaatgca attacgattg caagcttgat aagcgtgcta gatctggaga ctgcttttac     180
gatgctaaga gaaatcttca atgcatttgc gattactgcg aatactaa                  228
```

<210> SEQ ID NO 133
<211> LENGTH: 228
<212> TYPE: DNA
<213> ORGANISM: Artificial Sequence
<220> FEATURE:
<223> OTHER INFORMATION: E. coli pelB +Brazzein(H30R_E35D_E40D) gene

<400> SEQUENCE: 133

```
atgaaatacc tgctgccgac cgctgctgct ggtctgctgc tcctcgctgc ccagccggcg      60
atggccgata agtgcaagaa ggtttacgaa aattacccag tttctaagtg ccaacttgct     120
aatcaatgca attacgattg caagcttgat aagcgtgcta gatctggaga ctgcttttac     180
```

```
gatgacaaga gaaatcttca atgcatttgc gattactgcg aatactaa          228
```

<210> SEQ ID NO 134
<211> LENGTH: 228
<212> TYPE: DNA
<213> ORGANISM: Artificial Sequence
<220> FEATURE:
<223> OTHER INFORMATION: E. coli pelB +Brazzein(H30R_E35D_E40K) gene

<400> SEQUENCE: 134

```
atgaaatacc tgctgccgac cgctgctgct ggtctgctgc tcctcgctgc ccagccggcg    60
atggccgata agtgcaagaa ggtttacgaa aattacccag tttctaagtg ccaacttgct   120
aatcaatgca attacgattg caagcttgat aagcgtgcta gatctggaga ctgcttttac   180
gataaaaaga gaaatcttca atgcatttgc gattactgcg aatactaa              228
```

<210> SEQ ID NO 135
<211> LENGTH: 228
<212> TYPE: DNA
<213> ORGANISM: Artificial Sequence
<220> FEATURE:
<223> OTHER INFORMATION: E. coli pelB +Brazzein(H30R_E35D_E40R) gene

<400> SEQUENCE: 135

```
atgaaatacc tgctgccgac cgctgctgct ggtctgctgc tcctcgctgc ccagccggcg    60
atggccgata agtgcaagaa ggtttacgaa aattacccag tttctaagtg ccaacttgct   120
aatcaatgca attacgattg caagcttgat aagcgtgcta gatctggaga ctgcttttac   180
gatcgtaaga gaaatcttca atgcatttgc gattactgcg aatactaa              228
```

<210> SEQ ID NO 136
<211> LENGTH: 15
<212> TYPE: DNA
<213> ORGANISM: Artificial Sequence
<220> FEATURE:
<223> OTHER INFORMATION: syntheisized

<400> SEQUENCE: 136

```
gataagaaac gtgct                                                    15
```

<210> SEQ ID NO 137
<211> LENGTH: 66
<212> TYPE: DNA
<213> ORGANISM: Artificial Sequence
<220> FEATURE:
<223> OTHER INFORMATION: pelB signal sequence

<400> SEQUENCE: 137

```
atgaaatacc tgctgccgac cgctgctgct ggtctgctgc tcctcgctgc ccagccggcg    60
atggcc                                                              66
```

<210> SEQ ID NO 138
<211> LENGTH: 231
<212> TYPE: DNA
<213> ORGANISM: Artificial Sequence
<220> FEATURE:
<223> OTHER INFORMATION: E. coli pelB +Brazzein(29ins30 Lys_H30R_E35D_
      E40A) gene

<400> SEQUENCE: 138

```
atgaaatacc tgctgccgac cgctgctgct ggtctgctgc tcctcgctgc ccagccggcg    60
atggccgata agtgcaagaa ggtttacgaa aattacccag tttctaagtg ccaacttgct   120
aatcaatgca attacgattg caagcttgat aagaaacgtg ctagatctgg agactgcttt   180
```

```
tacgatgcta agagaaatct tcaatgcatt tgcgattact gcgaatacta a            231

<210> SEQ ID NO 139
<211> LENGTH: 231
<212> TYPE: DNA
<213> ORGANISM: Artificial Sequence
<220> FEATURE:
<223> OTHER INFORMATION: E. coli pelB +Brazzein(29ins30 Lys_H30R_E35D_
      E40D) gene

<400> SEQUENCE: 139
atgaaatacc tgctgccgac cgctgctgct ggtctgctgc tcctcgctgc ccagccggcg    60
atggccgata agtgcaagaa ggtttacgaa aattacccag tttctaagtg ccaacttgct   120
aatcaatgca attacgattg caagcttgat aagaaacgtg ctagatctgg agactgcttt   180
tacgatgaca agagaaatct tcaatgcatt tgcgattact gcgaatacta a            231

<210> SEQ ID NO 140
<211> LENGTH: 231
<212> TYPE: DNA
<213> ORGANISM: Artificial Sequence
<220> FEATURE:
<223> OTHER INFORMATION: E. coli pelB +Brazzein(29ins30 Lys_H30R_E35D_
      E40K) gene

<400> SEQUENCE: 140
atgaaatacc tgctgccgac cgctgctgct ggtctgctgc tcctcgctgc ccagccggcg    60
atggccgata agtgcaagaa ggtttacgaa aattacccag tttctaagtg ccaacttgct   120
aatcaatgca attacgattg caagcttgat aagaaacgtg ctagatctgg agactgcttt   180
tacgataaaa agagaaatct tcaatgcatt tgcgattact gcgaatacta a            231

<210> SEQ ID NO 141
<211> LENGTH: 231
<212> TYPE: DNA
<213> ORGANISM: Artificial Sequence
<220> FEATURE:
<223> OTHER INFORMATION: E. coli pelB +Brazzein(29ins30 Lys_H30R_E35D_
      E40R) gene

<400> SEQUENCE: 141
atgaaatacc tgctgccgac cgctgctgct ggtctgctgc tcctcgctgc ccagccggcg    60
atggccgata agtgcaagaa ggtttacgaa aattacccag tttctaagtg ccaacttgct   120
aatcaatgca attacgattg caagcttgat aagaaacgtg ctagatctgg agactgcttt   180
tacgatcgta agagaaatct tcaatgcatt tgcgattact gcgaatacta a            231

<210> SEQ ID NO 142
<211> LENGTH: 53
<212> TYPE: PRT
<213> ORGANISM: Artificial Sequence
<220> FEATURE:
<223> OTHER INFORMATION: Brazzein(H30R_E35D)

<400> SEQUENCE: 142

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Asp Lys Arg Ala Arg
            20                  25                  30

Ser Gly Asp Cys Phe Tyr Asp Glu Lys Arg Asn Leu Gln Cys Ile Cys
        35                  40                  45

Asp Tyr Cys Glu Tyr
```

<210> SEQ ID NO 143
<211> LENGTH: 53
<212> TYPE: PRT
<213> ORGANISM: Artificial Sequence
<220> FEATURE:
<223> OTHER INFORMATION: Brazzein(H30R_E40A)

<400> SEQUENCE: 143

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys Arg Ala Lys
            20                  25                  30

Ser Gly Glu Cys Phe Tyr Asp Ala Lys Arg Asn Leu Gln Cys Ile Cys
        35                  40                  45

Asp Tyr Cys Glu Tyr
        50

<210> SEQ ID NO 144
<211> LENGTH: 53
<212> TYPE: PRT
<213> ORGANISM: Artificial Sequence
<220> FEATURE:
<223> OTHER INFORMATION: Brazzein(H30R_E40D)

<400> SEQUENCE: 144

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys Arg Ala Lys
            20                  25                  30

Ser Gly Glu Cys Phe Tyr Asp Asp Lys Arg Asn Leu Gln Cys Ile Cys
        35                  40                  45

Asp Tyr Cys Glu Tyr
        50

<210> SEQ ID NO 145
<211> LENGTH: 53
<212> TYPE: PRT
<213> ORGANISM: Artificial Sequence
<220> FEATURE:
<223> OTHER INFORMATION: Brazzein(H30R_E40K)

<400> SEQUENCE: 145

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys Arg Ala Lys
            20                  25                  30

Ser Gly Glu Cys Phe Tyr Asp Lys Lys Arg Asn Leu Gln Cys Ile Cys
        35                  40                  45

Asp Tyr Cys Glu Tyr
        50

<210> SEQ ID NO 146
<211> LENGTH: 53
<212> TYPE: PRT
<213> ORGANISM: Artificial Sequence
<220> FEATURE:
<223> OTHER INFORMATION: Brazzein(H30R_E40R)

<400> SEQUENCE: 146

Asp Lys Cys Lys Lys Val Tyr Glu Asn Tyr Pro Val Ser Lys Cys Gln
1               5                   10                  15

-continued

Leu Ala Asn Gln Cys Asn Tyr Asp Cys Lys Leu Arg Lys Arg Ala Lys
            20                  25                  30

Ser Gly Glu Cys Phe Tyr Asp Arg Lys Arg Asn Leu Gln Cys Ile Cys
        35                  40                  45

Asp Tyr Cys Glu Tyr
        50

<210> SEQ ID NO 147
<211> LENGTH: 53
<212> TYPE: PRT
<213> ORGANISM: Artificial Sequence
<220> FEATURE:
<223> OTHER INFORMATION: Brazzein(E35D_E40A)

<400> SEQUENCE: 147

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Lys
            20                  25                  30

Ser Gly Asp Cys Phe Tyr Asp Ala Lys Arg Asn Leu Gln Cys Ile Cys
        35                  40                  45

Asp Tyr Cys Glu Tyr
        50

<210> SEQ ID NO 148
<211> LENGTH: 53
<212> TYPE: PRT
<213> ORGANISM: Artificial Sequence
<220> FEATURE:
<223> OTHER INFORMATION: Brazzein(E35D_E40D)

<400> SEQUENCE: 148

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Lys
            20                  25                  30

Ser Gly Asp Cys Phe Tyr Asp Asp Lys Arg Asn Leu Gln Cys Ile Cys
        35                  40                  45

Asp Tyr Cys Glu Tyr
        50

<210> SEQ ID NO 149
<211> LENGTH: 53
<212> TYPE: PRT
<213> ORGANISM: Artificial Sequence
<220> FEATURE:
<223> OTHER INFORMATION: Brazzein(E35D_E40K)

<400> SEQUENCE: 149

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Lys
            20                  25                  30

Ser Gly Asp Cys Phe Tyr Asp Lys Lys Arg Asn Leu Gln Cys Ile Cys
        35                  40                  45

Asp Tyr Cys Glu Tyr
        50

<210> SEQ ID NO 150
<211> LENGTH: 53
<212> TYPE: PRT

<213> ORGANISM: Artificial Sequence
<220> FEATURE:
<223> OTHER INFORMATION: Brazzein(E35D_E40R)

<400> SEQUENCE: 150

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Arg Lys His Ala Lys
            20                  25                  30

Ser Gly Asp Cys Phe Tyr Asp Arg Lys Arg Asn Leu Gln Cys Ile Cys
        35                  40                  45

Asp Tyr Cys Glu Tyr
        50

<210> SEQ ID NO 151
<211> LENGTH: 53
<212> TYPE: PRT
<213> ORGANISM: Artificial Sequence
<220> FEATURE:
<223> OTHER INFORMATION: Brazzein(H30R_E35D_E40A)

<400> SEQUENCE: 151

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Asp Lys Arg Ala Arg
            20                  25                  30

Ser Gly Asp Cys Phe Tyr Asp Ala Lys Arg Asn Leu Gln Cys Ile Cys
        35                  40                  45

Asp Tyr Cys Glu Tyr
        50

<210> SEQ ID NO 152
<211> LENGTH: 53
<212> TYPE: PRT
<213> ORGANISM: Artificial Sequence
<220> FEATURE:
<223> OTHER INFORMATION: Brazzein(H30R_E35D_E40D)

<400> SEQUENCE: 152

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Asp Lys Arg Ala Arg
            20                  25                  30

Ser Gly Asp Cys Phe Tyr Asp Asp Lys Arg Asn Leu Gln Cys Ile Cys
        35                  40                  45

Asp Tyr Cys Glu Tyr
        50

<210> SEQ ID NO 153
<211> LENGTH: 53
<212> TYPE: PRT
<213> ORGANISM: Artificial Sequence
<220> FEATURE:
<223> OTHER INFORMATION: Brazzein(H30R_E35D_E40K)

<400> SEQUENCE: 153

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Asp Lys Arg Ala Arg
            20                  25                  30

Ser Gly Asp Cys Phe Tyr Asp Lys Lys Arg Asn Leu Gln Cys Ile Cys
        35                  40                  45

Asp Tyr Cys Glu Tyr
    50

<210> SEQ ID NO 154
<211> LENGTH: 53
<212> TYPE: PRT
<213> ORGANISM: Artificial Sequence
<220> FEATURE:
<223> OTHER INFORMATION: Brazzein(H30R_E35D_E40R)

<400> SEQUENCE: 154

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Asp Lys Arg Ala Arg
            20                  25                  30

Ser Gly Asp Cys Phe Tyr Asp Arg Lys Arg Asn Leu Gln Cys Ile Cys
        35                  40                  45

Asp Tyr Cys Glu Tyr
    50

<210> SEQ ID NO 155
<211> LENGTH: 54
<212> TYPE: PRT
<213> ORGANISM: Artificial Sequence
<220> FEATURE:
<223> OTHER INFORMATION: Brazzein(29ins30 Lys_H30R_E35D_E40A)

<400> SEQUENCE: 155

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Asp Lys Lys Arg Ala
            20                  25                  30

Arg Ser Gly Asp Cys Phe Tyr Asp Ala Lys Arg Asn Leu Gln Cys Ile
        35                  40                  45

Cys Asp Tyr Cys Glu Tyr
    50

<210> SEQ ID NO 156
<211> LENGTH: 54
<212> TYPE: PRT
<213> ORGANISM: Artificial Sequence
<220> FEATURE:
<223> OTHER INFORMATION: Brazzein(29ins30 Lys_H30R_E35D_E40D)

<400> SEQUENCE: 156

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Asp Lys Lys Arg Ala
            20                  25                  30

Arg Ser Gly Asp Cys Phe Tyr Asp Asp Lys Arg Asn Leu Gln Cys Ile
        35                  40                  45

Cys Asp Tyr Cys Glu Tyr
    50

<210> SEQ ID NO 157
<211> LENGTH: 54
<212> TYPE: PRT
<213> ORGANISM: Artificial Sequence
<220> FEATURE:
<223> OTHER INFORMATION: Brazzein(29ins30 Lys_H30R_E35D_E40K)

<400> SEQUENCE: 157

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Asp Lys Lys Arg Ala
            20                  25                  30

Arg Ser Gly Asp Cys Phe Tyr Asp Lys Lys Arg Asn Leu Gln Cys Ile
        35                  40                  45

Cys Asp Tyr Cys Glu Tyr
    50

<210> SEQ ID NO 158
<211> LENGTH: 54
<212> TYPE: PRT
<213> ORGANISM: Artificial Sequence
<220> FEATURE:
<223> OTHER INFORMATION: Brazzein(29ins30 Lys_H30R_E35D_E40R)

<400> SEQUENCE: 158

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Asp Lys Lys Arg Ala
            20                  25                  30

Arg Ser Gly Asp Cys Phe Tyr Asp Arg Lys Arg Asn Leu Gln Cys Ile
        35                  40                  45

Cys Asp Tyr Cys Glu Tyr
    50

<210> SEQ ID NO 159
<211> LENGTH: 162
<212> TYPE: DNA
<213> ORGANISM: Artificial Sequence
<220> FEATURE:
<223> OTHER INFORMATION: Brazzein

<400> SEQUENCE: 159
gataagtgca agaaggttta cgaaaattac ccagtttcta agtgccaact tgctaatcaa      60
tgcaattacg attgcaagct tgctaagcat gctagatctg gagaatgctt ttacgatgaa     120
aagagaaatc ttcaatgcat ttgcgattac tgcgaatact aa                        162

<210> SEQ ID NO 160
<211> LENGTH: 30
<212> TYPE: DNA
<213> ORGANISM: Artificial Sequence
<220> FEATURE:
<223> OTHER INFORMATION: forward primer for brazzein cloning

<400> SEQUENCE: 160
catgccatgg ataagtgcaa gaaggtttac                                       30

<210> SEQ ID NO 161
<211> LENGTH: 28
<212> TYPE: DNA
<213> ORGANISM: Artificial Sequence
<220> FEATURE:
<223> OTHER INFORMATION: reverse primer for brazzein cloning

<400> SEQUENCE: 161
ccgctcgagt tagtattcgc agtaatcg                                         28

<210> SEQ ID NO 162
<211> LENGTH: 30
<212> TYPE: DNA
<213> ORGANISM: Artificial Sequence
<220> FEATURE:

-continued

```
<223> OTHER INFORMATION: ATG deletion primer 1

<400> SEQUENCE: 162
cagccggcga tggccgacaa atgcaaaaaa                                    30

<210> SEQ ID NO 163
<211> LENGTH: 30
<212> TYPE: DNA
<213> ORGANISM: Artificial Sequence
<220> FEATURE:
<223> OTHER INFORMATION: ATG deletion primer 2

<400> SEQUENCE: 163 tttttttgcat ttgtcggcca tcgccggctg                                   30
```

BRAZZEIN VARIANT HAVING HIGHER SWEETNESS AND METHOD FOR PREPARING MULTI-VARIANT

RELATED APPLICATIONS

This application is a 35 U.S.C. §371 national phase application of PCT/KR2009/004855 (WO 2011/025077), filed on Aug. 28, 2009, entitled "NOVEL BRAZZEIN VARIANT HAVING HIGHER SWEETNESS AND METHOD FOR PREPARING MULTI-VARIANT", which is incorporated herein by reference in its entirety.

Incorporated by reference herein in its entirety is the Sequence Listing entitled "[G110303P US 0338.19 PCT-US] ST25.txt," which was created Jul. 8, 2013, size 67 kilobyte.

FIELD OF THE INVENTION

The present invention relates to a novel brazzein multi-variant having high sweetness and the use thereof, and more particularly, to a brazzein variant having higher sweetness than minor types of a wild-type brazzein protein, a method of preparing the same, and a food composition for enhancing a sugar content comprising the same.

DISCUSSION OF RELATED ART

White sugar (refined sugar) is a disaccharide referred to as a kind of saccharose (a chemical term referring to sugar) composed of a simple carbohydrate called "sucrose." Sugar has been frequently used as a sweetener for a long period of time. However, the World Health Organization (WHO) has proposed a recommendation to limit the use of sugar to 10% of the recent consumption because of problems of sugar such as harmfulness to the human body, and state governments of the United States have prohibited to sell foods including sugar as a major ingredient and drinks including a high content of sugar (July 2003 in New York City, September 2004 in New Jersey, March 2006 in Illinois, and April 2006 in Connecticut). In Korea, the National Obesity Taskforce has also been organized to announce to sugar manufacturers to mark warning labels about sugar risks on their products, and scheduled to regulate advertisements for foods containing sugar exceeding a standard sugar content after 2010. Therefore, there is a need to develop a new sweetener that can be substituted for sugar.

In 1879, Ira Remsen (USA) and Constantin Fahlberg (Germany) discovered saccharin, which is considered to be approximately 500 times sweeter than sugar. Saccharin has an advantage in that it is not digested in the human body but excreted from the human body. However, there is controversy over whether saccharin is a carcinogenic substance. Finally, although saccharin was proven to be harmless to the human body, it is still hardly used due to its bitter aftertaste. In 1937, the University of Illinois (USA) found that sodium cyclohexylsulfamate has a sweet taste. With the trade name cyclamate, it was first used in the beginning of 1950, and swept through the global sweetener market in the 1960s. However, as the sodium cyclohexylsulfamate was proven to be a carcinogenic substance, it has been completely prohibited since the 1970s in Korea. An artificial sweetener most widely used in recent years is aspartame that was discovered in 1965 by James Schlatter. Aspartame has a sugar content approximately 180 to 200 times that of sugar. Aspartame is included in a majority of currently commercially available diet drinks, and thus is subjected to a metabolic pathway to generate phenylalanine when it is taken up into the human body. Therefore, because of a congenital deficiency in the enzyme that serves to break down phenylalanine, i.e., phenylalanine hydroxylase, phenylketonuric patients cannot use the enzyme.

There has been continuous research conducted to develop not only artificial sweeteners but also natural sweeteners. As a result, a compound referred to as stevioside was found to be present in the leaves of a perennial plant (i.e., *Stevia rebaudiana*) in the aster family, which is classified as an herb. The natives living in the border between Paraguay and Brazil have used stevioside as a sweetener for over 400 years. In Korea, stevioside is sometimes added to a traditional distilled liquor called "soju" and is 200 times as sweet as sugar.

Meanwhile, increasing attention has been paid to a sweetener protein extracted from a tropical fruit. Thaumatin is a kind of protein included in the fruit of a perennial plant (i.e., *Thaumatococcus daniellii*) referred to as a miracle fruit in Western Africa, and is 2,000 to 3,000 times as sweet as sugar. Monellin is a protein obtained from the fruit of a viny plant called a serendipity berry growing in the rain forest area of Africa, and is 3,000 times as sweet as sugar. However, it is very difficult to cultivate the serendipity berry and also to extract monellin from its fruit. Moreover, monellin has a problem in that it has low thermal stability. Therefore, when monellin is heat-treated in a food processing process, it does not show sweetness due to the breakdown of its 3-dimensional protein structure. In order to solve these problems, there has been research conducted to enhance the thermal stability of the monellin using a protein engineering technique.

Meanwhile, brazzein is a sweetener protein extracted from the fruit of *Pentadiplandra brazzeana* (Baillon) growing in West Africa (Ming et al., *FEBS Letters*, 355: 106-108, 1994). Brazzein shows sweetness approximately 500 to 2,000 times that of sucrose (Jin et al., *Chem. Senses*. 28: 491-498, 2003), and is divided into two types: a major type and a minor type. The major type accounting for a majority of brazzein extracted from the plant has 54 amino acids including a pyroglutamic acid residue bound to an amino-terminal region. On the other hand, the minor type of brazzein has 53 amino acid residues without a pyroglutamic acid residue bound to an amino-terminal region, and shows stronger sweetness, approximately twice that of the major type of brazzein (Assadi-Porter et al., *Arch., Biochem. Biophys*. 376: 259-265, 2000). Brazzein has a molecular weight of approximately 6.5 kDa, which is the smallest among the sweetener proteins, and is a monomer composed of one kind of subunit. Also, brazzein consists of a single polypeptide and has one α-helix and two β-pleated sheets. Brazzein has very high thermal stability since it has 8 cysteine residues to form 4 disulfide bonds in the molecule. Also, brazzein shows very high solubility and pH stability in water (Gao et al., *Int. J. Biol. macromol*. 24: 351-359, 1999).

U.S. Pat. No. 6,274,707 B1 and Assadi-Porter et al. (Assadi-Porter et al., Arch. Biochem. Biophys. 376: 259-265, 2000) disclose a method of producing recombinant brazzein using a genetic engineering method by which the above-described brazzein is produced in *Escherichia coli* (*E. coli*). Here, the method includes synthesizing a gene coding for brazzein, inserting the gene into a recombinant vector containing a SNase gene to construct a new transformation vector, introducing the transformation vector into *E. coli*, and expressing and finally purifying a fusion protein linked with the SNase. However, the brazzein fused and expressed with the SNase is produced as an insoluble inclusion body. Therefore, the insoluble inclusion body should be refolded, separated and purified by removing SNase and methionine (Met)

using cyanobromide (CNBr). Therefore, it is very difficult to commercialize the recombinant brazzein since it may not be mass-produced due to technically complex and very difficult processes. Accordingly, the present inventors have conducted research to solve the prior-art problems, and filed an application disclosing a polynucleotide including an *E. coli* pelB signal sequence and a brazzein gene and a method of preparing brazzein using the same (Korean Patent Application No. 2006-97619).

Therefore, in order to search for a natural sweetener showing high thermal stability and excellent sweetness, the present inventors have prepared variants and multi-variants by mutating wild-type brazzein through substitution of amino acids at certain positions which are expected not to affect a structure in an amino acid sequence of brazzein, and screening a brazzein variant or multi-variant having equivalent properties such as thermal stability, pH stability and high water solubility and showing higher sweetness compared to the conventional brazzein. Therefore, the present invention was completed based on the above-described facts.

DISCLOSURE

Technical Problem

The present invention is directed to providing a novel brazzein variant or multi-variant having equivalent properties such as high thermal and pH stabilities and high water solubility compared to a minor-type protein of the conventional brazzein and showing stronger sweetness at least 2 times and up to 20 times that of the minor-type protein.

Technical Solution

One aspect of the present invention provides a novel brazzein variant having more excellent sweetness than a conventional wild-type brazzein.

Another aspect of the present invention provides a polynucleotide coding for the brazzein variant or multi-variant.

Still another aspect of the present invention provides a recombinant expression vector including the polynucleotide, an *E. coli* strain transformed with the recombinant expression vector, and a method of preparing a brazzein variant using the *E. coli* strain.

Yet another aspect of the present invention provides a food composition for enhancing a sugar content including the brazzein variant or multi-variant as an effective component.

Hereinafter, the present invention will be described in detail.

The present invention is directed to providing a novel brazzein variant or multi-variant having a higher sugar content than a conventional wild-type brazzein.

According to one exemplary embodiment of the present invention, 40 recombinant vectors coding for brazzein variants are constructed using site-directed mutagenesis by substituting a $5^{th}$ amino acid residue (lysine), a $28^{th}$ amino acid residue (aspartic acid), a $30^{th}$ amino acid residue (histidine), a $35^{th}$ amino acid residue (glutamic acid), a $40^{th}$ amino acid residue (glutamic acid) or a $42^{nd}$ amino acid residue (arginine) of minor-type brazzein with other amino acids.

According to another exemplary embodiment of the present invention, the recombinant vectors constructed thus are used to express brazzein variants, and the expressed brazzein variants are purified to obtain high-purity brazzein variants.

According to still another exemplary embodiment of the present invention, the activities (sweetness) and thermal stabilities of the brazzein variants prepared thus and a minor-type brazzein protein are measured. As a result, the brazzein variants, in which a $30^{th}$ amino acid residue (histidine) and a $35^{th}$ amino acid residue (glutamic acid) of the minor-type brazzein protein are substituted with arginine and aspartic acid residues, respectively, and a $40^{th}$ glutamic acid residue is substituted with alanine, aspartic acid, lysine or arginine residue, have a higher activity (sweetness) and an equivalent thermal stability compared to the minor-type brazzein protein. Therefore, the brazzein variants are selected to prepare brazzein multi-variants showing higher sweetness, but it can be seen that the brazzein variants themselves may be used as an excellent sweetener.

According to yet another exemplary embodiment of the present invention, the brazzein variants prepared thus are properly combined to construct 17 recombinant vectors coding for brazzein multi-variants including 9 secondary brazzein variants, 4 tertiary brazzein variants and 4 quaternary brazzein variants obtained by inserting a lysine residue between a $29^{th}$ lysine residue and a $30^{th}$ histidine residue of the minor-type brazzein on the basis of the tertiary brazzein variants. Then, the brazzein variants are expressed from the 17 recombinant vectors, purified and measured for activities (sweetness) in the same manner as in the above-described exemplary embodiments. As a result, it is possible to obtain high-purity brazzein variants, and to prepare brazzein variants having an equivalent stability to the minor-type brazzein protein and showing higher sweetness at least 4 and up to 20 times that of the minor-type brazzein protein. From these facts, it can be seen that the brazzein multi-variants prepared using the screened brazzein variants are also used as an excellent sweetener.

Therefore, the present invention is directed to providing a brazzein variant in which a $30^{th}$ amino acid residue (histidine), a $35^{th}$ amino acid residue (glutamic acid) or a $40^{th}$ amino acid residue (glutamic acid) of the minor-type brazzein is substituted with one of other amino acids.

According to one exemplary embodiment, the brazzein variant according to the present invention may be, for example, a brazzein variant having an amino acid sequence set forth in SEQ ID NO: 100 in which a $30^{th}$ amino acid residue, histidine, is substituted with an arginine residue, a brazzein variant having an amino acid sequence set forth in SEQ ID NO: 109 in which a $35^{th}$ amino acid residue, glutamic acid, is substituted with an aspartic acid residue, or a brazzein variant having an amino acid sequence set forth in SEQ ID NO: 113, SEQ ID NO: 114, SEQ ID NO: 115 or SEQ ID NO: 117 in which a $40^{th}$ glutamic acid residue is substituted with an alanine residue, an aspartic acid residue, a lysine residue or an arginine residue, respectively.

According to another exemplary embodiment, the brazzein variant according to the present invention may be a brazzein multi-variant in which at least two of the $30^{th}$ amino acid residue (histidine), the $35^{th}$ amino acid residue (glutamic acid) and the $40^{th}$ amino acid residue (glutamic acid) are substituted, for example a brazzein variant having an amino acid sequence set forth in SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153 or SEQ ID NO: 154.

Also, the brazzein variant according to the present invention may be obtained by inserting a lysine residue between a $29^{th}$ lysine residue and a $30^{th}$ histidine residue of the brazzein variant having an amino acid sequence set forth in SEQ ID NO: 151, SEQ ID NO: 152, SEQ ID NO: 153 or SEQ ID NO:

154, and may preferably have an amino acid sequence set forth in SEQ ID NO: 155, SEQ ID NO: 156, SEQ ID NO: 157 or SEQ ID NO: 158.

Meanwhile, the present invention is directed to providing a polynucleotide coding for the brazzein variant. The polynucleotide may be a polynucleotide coding for an amino acid sequence set forth in SEQ ID NO: 100, SEQ ID NO: 109, SEQ ID NO: 113, SEQ ID NO: 114, SEQ ID NO: 115 or SEQ ID NO: 117, and may preferably have a base sequence set forth in SEQ ID NO: 59 for an amino acid sequence set forth in SEQ ID NO: 100, a base sequence set forth in SEQ ID NO: 68 for an amino acid sequence set forth in SEQ ID NO: 109, a base sequence set forth in SEQ ID NO: 72 for an amino acid sequence set forth in SEQ ID NO: 113, a base sequence set forth in SEQ ID NO: 73 for an amino acid sequence set forth in SEQ ID NO: 114, a base sequence set forth in SEQ ID NO: 74 73 for an amino acid sequence set forth in SEQ ID NO: 115, or a base sequence set forth in SEQ ID NO: 76 for an amino acid sequence set forth in SEQ ID NO: 117.

Also, the polynucleotide coding for the brazzein multi-variant according to the present invention may be a polynucleotide coding for an amino acid sequence set forth in SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157 or SEQ ID NO: 158, and may preferably have a base sequence set forth in SEQ ID NO: 123 for an amino acid sequence set forth in SEQ ID NO: 142, a base sequence set forth in SEQ ID NO: 124 123 for an amino acid sequence set forth in SEQ ID NO: 143, a base sequence set forth in SEQ ID NO: 125 for an amino acid sequence set forth in SEQ ID NO: 144, a base sequence set forth in SEQ ID NO: 126 for an amino acid sequence set forth in SEQ ID NO: 145, a base sequence set forth in SEQ ID NO: 127 for an amino acid sequence set forth in SEQ ID NO: 146, a base sequence set forth in SEQ ID NO: 128 for an amino acid sequence set forth in SEQ ID NO: 147, a base sequence set forth in SEQ ID NO: 129 for an amino acid sequence set forth in SEQ ID NO: 148, a base sequence set forth in SEQ ID NO: 130 for an amino acid sequence set forth in SEQ ID NO: 149, a base sequence set forth in SEQ ID NO: 131 for an amino acid sequence set forth in SEQ ID NO: 150, a base sequence set forth in SEQ ID NO: 132 for an amino acid sequence set forth in SEQ ID NO: 151, a base sequence set forth in SEQ ID NO: 133 for an amino acid sequence set forth in SEQ ID NO: 152, a base sequence set forth in SEQ ID NO: 134 for an amino acid sequence set forth in SEQ ID NO: 153, a base sequence set forth in SEQ ID NO: 135 for an amino acid sequence set forth in SEQ ID NO: 154, a base sequence set forth in SEQ ID NO: 138 for an amino acid sequence set forth in SEQ ID NO: 155, a base sequence set forth in SEQ ID NO: 139 for an amino acid sequence set forth in SEQ ID NO: 156, a base sequence set forth in SEQ ID NO: 140 for an amino acid sequence set forth in SEQ ID NO: 157, or a base sequence set forth in SEQ ID NO: 141 for an amino acid sequence set forth in SEQ ID NO: 158.

In addition, the present invention is directed to providing a recombinant expression vector for expression of a brazzein variant or multi-variant including a promoter and the polynucleotide operably linked with the promoter.

The term "promoter" refers to a DNA sequence to which a nucleic acid sequence is operably linked to control expression of the nucleic acid sequence in a certain host cell, and the term "operably linked" means that one nucleic acid fragment is bound to another nucleic acid fragment such that functions and expression of the one nucleic acid fragment are affected by the latter nucleic acid fragment. In addition, the promoter may further include an optional operator sequence configured to control transcription, a sequence encoding a suitable mRNA ribosome-binding site, and sequences controlling the termination of transcription and translation. Here, the promoter may be a constitutive promoter which constitutively induces the expression of a target gene constantly, or an inducible promoter which induces the expression of a target gene at a specific site for a specific time. Examples of the promoter include an *E. coli* pelB promoter, a U6 promoter, a cytomegalovirus (CMV) promoter, an SV40 promoter, a CAG promoter (Hitoshi Niwa et al., Gene, 108:193-199, 1991; Monahan et al., *Gene Therapy*, 7:24-30, 2000), a CaMV $^{35}$S promoter (Odell et al., Nature 313:810-812, 1985), an Rsyn7 promoter (U.S. patent application Ser. No. 08/991,601), a rice actin promoter (McElroy et al., *Plant Cell* 2:163-171, 1990), a ubiquitin promoter (Christensen et al., *Plant Mol. Biol.* 12:619-632, 1989), and an ALS promoter (U.S. patent application Ser. No. 08/409,297). In addition to the promoters, promoters disclosed in U.S. Pat. Nos. 5,608, 149; 5,608,144, 5,604,121, 5,569,597, 5,466,785, 5,399,680, 5,268,463 and 5,608,142 may be used herein. An *E. coli* pelB promoter may be preferably used as the promoter.

The *E. coli* pelB signal sequence is a kind of periplasmic signal sequence derived from *E. coli* (Rietsch et al., *Proc. Natl. Acad. Sci. USA*, 93: 130408-13053, 1996, Raina et al., *Ann. Rev. Microbiol.* 51: 179-202, 1997, Sone et al., *J. Biol. Chem.* 272: 10349-10352, 1997). When the brazzein according to the present invention is synthesized, the *E. coli* pelB signal sequence may serve to translocate the brazzein into the *E. coli* periplasm and induce formation of an exact disulfide bond, to inhibit formation of an insoluble inclusion body of a brazzein protein, and to facilitate a purification process by minimizing unnecessary expression of *E. coli*-derived proteins. The *E. coli* pelB signal sequence according to the present invention preferably has a base sequence set forth in SEQ ID NO: 137, and is linked to a 5' upstream end of a nucleotide sequence of the brazzein variant according to the present invention so that it can have the same frame upon translation into a protein.

According to the present invention, the term "recombinant expression vector" refers to a vector that can express a target protein or transcribe a target RNA in a host cell, and also to a gene construct that includes an essential regulatory factor operably linked thereto to express a gene insert.

The vector according to the present invention includes a plasmid vector, a cosmid vector, a bacteriophage vector and a viral vector, but the present invention is not particularly limited thereto. In addition to the expression control sequences such as a promoter, an operator, an initiation codon, a termination codon, a polyadenylation signal and an enhancer, a suitable expression vector may include a signal or leader sequence for membrane targeting or secretion, and be prepared through various methods, when necessary. Also, the expression vector includes a selection marker for selecting a host cell with the vector, and a replication origin when it is a replicable expression vector.

As such, the recombinant expression vector for expression of the brazzein variant according to the present invention may be preferably pET26B(+)-Brazzein(H30R), pET26B(+)-Brazzein(E35D), pET26B(+)-B razzein(E40A), pET26B(+)-Brazzein(E40D), pET26B(+)-Brazzein(E40K) or pET26B(+)-Brazzein(E40R), which may be constructed through site-directed mutagenesis using pET26B(+)-Brazzein(Met-) as a template and SEQ ID NO: 19 for pET26B(+)-Brazzein (H30R), SEQ ID NO: 28 for pET26B(+)-Brazzein(E35D), SEQ ID NO: 32 for pET26B(+)-Brazzein(E40A), SEQ ID NO: 33 for pET26B(+)-Brazzein(E40D), SEQ ID NO: 34 for pET26B(+)-Brazzein(E40K), or SEQ ID NO: 36 for pET26B (+)-Brazzein(E40R).

As such, the recombinant expression vector for expression of the secondary brazzein variant out of the brazzein multi-variants according to the present invention may also be preferably pET26B(+)-Brazzein(H30R_E35D), pET26B(+)-Brazzein(H30R_E40A), pET26B(+)-Brazzein (H30R_E40D), pET26B(+)-Brazzein(H30R_E40K) or pET26B(+)-Brazzein(H30R_E40R), which may be constructed through site-directed mutagenesis using pET26B (+)-Brazzein(H30R) as a template and SEQ ID NO: 28 for pET26B(+)-Brazzein(H30R_E35D), SEQ ID NO: 32 for pET26B(+)-Brazzein(H30R_E40A), SEQ ID NO: 33 for pET26B(+)-Brazzein(H30R_E40D), SEQ ID NO: 34 for pET26B(+)-Brazzein(H30R_E40K), or SEQ ID NO: 36 for pET26B(+)-Brazzein(H30R_E40R).

As such, the recombinant expression vector for expression of the other secondary brazzein variant out of the brazzein multi-variants according to the present invention may also be preferably pET26B(+)-Brazzein(E35D_E40A), pET26B(+)-Brazzein(E35D_E40D), pET26B(+)-Brazzein (E35D_E40K) or pET26B(+)-Brazzein(E35D_E40R), which may be constructed through site-directed mutagenesis using pET26B(+)-Brazzein(E35D) as a template and SEQ ID NO: 32 for pET26B(+)-Brazzein(E35D_E40A), SEQ ID NO: 33 for pET26B(+)-Brazzein(E35D_E40D), SEQ ID NO: 34 for pET26B(+)-Brazzein(E35D_E40K), or SEQ ID NO: 36 for pET26B(+)-Brazzein(E35D_E40R).

As such, the recombinant expression vector for expression of the tertiary brazzein variant out of the brazzein multi-variants according to the present invention may also be preferably pET26B(+)-Brazzein(H30R_E35D_E40A), pET26B (+)-Brazzein(H30R_E35D_E40D), pET26B(+)-Brazzein (H30R_E35D_E40K) or pET26B(+)-Brazzein (H30R_E35D_E40R), which may be constructed through site-directed mutagenesis using pET26B(+)-Brazzein (H30R_E35D) as a template and SEQ ID NO: 32 for pET26B (+)-Brazzein(H30R_E35D_E40A), SEQ ID NO: 33 for pET26B(+)-Brazzein(H30R_E35D_E40D), SEQ ID NO: 34 for pET26B(+)-Brazzein(H30R_E35D_E40K), or SEQ ID NO: 36 for pET26B(+)-Brazzein(H30R_E35D_E40R).

As such, the recombinant expression vector for expression of the quaternary brazzein variant out of the brazzein multi-variants according to the present invention may also be preferably pET26B(+)-Brazzein(29-ins30 Lys_H30R_E35D_E40A), pET26B(+)-Brazzein(29-ins30 Lys_H30R_E35D_E40D), pET26B(+)-Brazzein(29-ins30 Lys_H30R_E35D_E40K) or pET26B(+)-Brazzein(29-ins30 Lys_H30R_E35D_E40R), which may be constructed through site-directed mutagenesis using SEQ ID NO: 136 as a primer and pET26B(+)-Brazzein(H30R_E35D_E40A), pET26B(+)-Brazzein(H30R_E35D_E40D), pET26B(+)-Brazzein(H30R_E35D_E40K), or pET26B(+)-Brazzein (H30R_E35D_E40R) as a template for pET26B(+)-Brazzein (29-ins30 Lys_H30R_E35D_E40A), pET26B(+)-Brazzein (29-ins30 Lys_H30R_E35D_E40D), pET26B(+)-Brazzein (29-ins30 Lys_H30R_E35D_E40K), or pET26B(+)-Brazzein(29-ins30 Lys_H30R_E35D_E40R), respectively.

Also, the present invention is directed to providing an *E. coli* strain including the recombinant expression vector. The *E. coli* strain is transformed with the recombinant expression vector according to conventional transformation methods. In this case, the transformation may be performed using a suitable standard technique according to the kind of host cells known in the art, including any methods of introducing a nucleic acid into a host cell. Such a standard technique includes electroporation, calcium phosphate ($CaPO_4$) precipitation, calcium chloride ($CaCl_2$) precipitation, microprojectile bombardment, PEG-mediated fusion, microinjection, and a liposome-mediated method, but the present invention is not limited thereto.

The present invention is directed to providing a method of preparing a brazzein variant. Here, the method according to the present invention includes culturing the transformed *E. coli* strain, isolating a periplasmic protein from the cultured *E. coli* strain, and heat-treating the isolated periplasmic protein to purify brazzein.

The *E. coli* strain transformed to include the polynucleotide according to the present invention may be cultured in a suitable medium under the suitable conditions to express a polynucleotide encoding a brazzein variant. Here, the culture conditions are identical or similar to the conventional conditions used to culture an *E. coli* strain. As the transformed *E. coli* strain is cultured, a brazzein protein containing a pelB signal sequence is expressed under control of an expression control sequence in the expression vector. According to the present invention, such expression of the brazzein is performed without using a compound, such as isopropyl-beta-D-thiogalactopyranoside (IPTG), which facilitates the expression of a conventional inducible promoter. The expressed brazzein containing the pelB signal sequence is translocated into the *E. coli* periplasm by the action of the signal sequence, and the signal sequence is removed by an *E. coli* signal peptidase to synthesize brazzein.

In order to isolate the brazzein expressed in the transformed cell from the *E. coli* periplasm, a known method of isolating a protein from the *E. coli* periplasm (Snyder et al., *J. Bacteriology*, 177: 953963, 1995) may be used, but the present invention is not limited thereto. For example, the isolation method may be performed by collecting the cultured *E. coli* strain, suspending the collected *E. coli* strain in a 30 mM Tri-HCl (pH 8) solution supplemented with 20% sucrose and eluting an *E. coli* periplasmic protein using an EDTA (pH 8) solution and $MgSO_4$.

The method of isolating the brazzein according to the present invention from the *E. coli* periplasmic protein may be performed using various isolation and purification methods known in the art. For example, the brazzein according to the present invention may be isolated using techniques such as salting out (ammonium sulfate precipitation and sodium phosphate precipitation), solvent precipitation (precipitation of a protein fraction using acetone or ethanol), dialysis, gel filtration, ion exchange chromatography, reverse phase column chromatography and affinity chromatography, which may be used alone or in combination. Since the brazzein according to the present invention is stable to heat, the method of isolating the brazzein may be preferably performed using heat treatment. The heat treatment may be preferably performed by heating a cell homogenate at 70 to 90° C. for 15 to 60 minutes to thermally denature proteins other than the brazzein and centrifuging the cell homogenate at 4° C. and 18,000 g for 30 minutes to isolate the thermally denatured proteins and the brazzein, but the present invention is not limited thereto.

For reference, the above-described nucleotide and protein works may be carried out with reference to the following documents (Maniatis et al., Molecular Cloning: A Laboratory Manual, Cold Spring Harbor Laboratory, Cold Spring Harbor, N.Y. (1982); Sambrook et al., Molecular Cloning: A Laboratory Manual, 2d Ed., Cold Spring Harbor Laboratory Press (1989); Deutsher, M., Guide to Protein Purification Methods Enzymology, vol. 182. Academic Press. Inc., San Diego, Calif. (1990)).

As described above, the enzymological properties of the brazzein variant according to the present invention having an amino acid sequence set forth in SEQ ID NO: 100, SEQ ID NO: 109, SEQ ID NO: 113, SEQ ID NO: 114, SEQ ID NO: 115 or SEQ ID NO: 117; and the brazzein multi-variant according to the present invention having an amino acid sequence set forth in SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157 or SEQ ID NO: 158, which have higher sweetness and high thermal stability, are summarized as follows.

1) Molecular weight: 6.5 kDa
2) High thermal stability and acid resistance
3) High water solubility
4) Brazzein variants having higher sweetness at least 2 to 3.3 times that of a brazzein protein of a minor-type brazzein
5) Brazzein variants having higher sweetness at least approximately 4,000 to approximately 6,600 times that of 1 g/100 ml of sucrose
6) Brazzein multi-variants having higher sweetness at least 4 to 20 times that of a brazzein protein of a minor-type brazzein
7) Brazzein multi-variants having higher sweetness at least approximately 8,000 to approximately 40,000 times that of 1 g/100 ml of sucrose As such, comparing the brazzein variant or multi-variant according to the present invention to a minor-type brazzein protein expressed and purified as disclosed in Korean Patent Application No. 2006-97619 filed by the same applicant as the present invention, that is, a wild-type minor-type brazzein protein, and a brazzein variant expressed and purified as disclosed in Korean Patent Application No. 10-2007-0117013, the brazzein variant according to the present invention and the brazzein multi-variant prepared based on the brazzein variant have novel amino acid sequences so that they can have equivalent properties such as thermal stability, acid resistance and water solubility and show higher sweetness, compared to the wild-type brazzein.

According to the present invention, the brazzein variant also shows higher sweetness than a brazzein variant known in U.S. Pat. Nos. 6,274,707B 1 and 7,153,535, and has other effects.

Therefore, the brazzein variant according to the present invention may be used instead of a natural sweetener such as sugar, fructose or oligosaccharide or an artificial sweetener such as aspartame. Accordingly, the present invention is also directed to providing the use of the brazzein variant for production of a sweetener, the use of the brazzein variant for enhancing a sugar content in food, a sweetener including the brazzein variant, and a food composition including the brazzein variant as a sweetener.

The food composition according to the present invention includes all kinds of a functional food, a nutritional supplement, a health food and a food additive. These kinds of food compositions may be prepared into various formulations using conventional methods known in the art.

For example, the formulations may be prepared by adding the brazzein variant according to the present invention to beverages (including alcoholic beverages), fruits and their processed foods (for example, canned fruit, bottled fruit, jam, marmalade, etc.), fishes, meats and their processed foods (for example, ham, sausage, corned beef, etc.), breads and noodles (for example, udon, buckwheat noodles, ramen, spaghetti, macaroni, etc.), fruit juices, various drinks, cookies, wheat-gluten, dairy products (for example, butter, cheese, etc.), edible vegetable fats and oils, margarine, vegetable proteins, retort foods, frozen foods, various condiments (for example, soybean paste (doenjang), soy sauce, sauces, etc.).

In addition, the food composition including the brazzein variant according to the present invention may be prepared in the form of a powder or concentrated solution, and used as a food additive such as a sweetener.

In the food composition according to the present invention, the brazzein variant according to the present invention may be preferably included at a content of approximately 0.01 to 10% by weight, based on the total weight of the food composition.

Effects of the Invention

As described above, the brazzein variant according to the present invention has excellent properties such as thermal stability, acid resistance and water solubility compared to a conventional brazzein and also shows higher sweetness at least 2 times and up to 3.3 times that of the conventional brazzein. Like the brazzein variant, the brazzein multi-variant according to the present invention also has the same stability as the minor-type brazzein protein and shows higher sweetness at least 4 times and up to 20 times that of the minor-type brazzein protein. Therefore, the brazzein variant according to the present invention may be widely used as a sweetener in food compositions since a greater amount of other sweeteners may be replaced with a smaller amount of the brazzein variant.

BRIEF DESCRIPTION OF THE DRAWINGS

FIGS. 2 to 4 are schematic diagrams illustrating a process for constructing a brazzein variant and a brazzein multi-variant according to the present invention.

FIG. 5 shows the thermal stability results of brazzein variants showing high sweetness, which are screened after measuring the sweetness of the brazzein variants according to the present invention.

Lane 1: Relative activity of minor-type brazzein after heat treatment
Lane 2: Relative activity of a brazzein variant (H30K) after heat treatment
Lane 3: Relative activity of a brazzein variant (H30R) after heat treatment
Lane 4: Relative activity of a brazzein variant (E35D) after heat treatment
Lane 5: Relative activity of a brazzein variant (E40A) after heat treatment
Lane 6: Relative activity of a brazzein variant (E40D) after heat treatment
Lane 7: Relative activity of a brazzein variant (E40K) after heat treatment
Lane 8: Relative activity of a brazzein variant (E40H) after heat treatment
Lane 9: Relative activity of a brazzein variant (E40R) after heat treatment FIG. 6 shows the electrophoresis results to determine expression of brazzein multi-variants according to the present invention.

Lane M: Molecular weight marker
Lane 1: Purified secondary brazzein variant (H30R_E35D)
Lane 2: Purified secondary brazzein variant (H30R_E40A)
Lane 3: Purified secondary brazzein variant (H30R_E40D)
Lane 4: Purified secondary brazzein variant (H30R_E40K)

Lane 5: Purified secondary brazzein variant (H30R_E40R)
Lane 6: Purified secondary brazzein variant (E35D_E40A)
Lane 7: Purified secondary brazzein variant (E35D_E40D)
Lane 8: Purified secondary brazzein variant (E35D_E40K)
Lane 9: Purified secondary brazzein variant (E35D_E40R)
Lane 10: Purified tertiary brazzein variant (H30R_E35D_E40A)
Lane 11: Purified tertiary brazzein variant (H30R_E35D_E40D)
Lane 12: Purified tertiary brazzein variant (H30R_E35D_E40K)
Lane 13: Purified tertiary brazzein variant (H30R_E35D_E40R)
Lane 14: Purified quaternary brazzein variant (29-ins30 Lys_H30R_E35D_E40A)
Lane 15: Purified quaternary brazzein variant (29-ins30 Lys_H30R_E35D_E40D)
Lane 16: Purified quaternary brazzein variant (29-ins30 Lys_H30R_E35D_E40K)
Lane 17: Purified quaternary brazzein variant (29-ins30 Lys_H30R_E35D_E40R)

Figure 7:
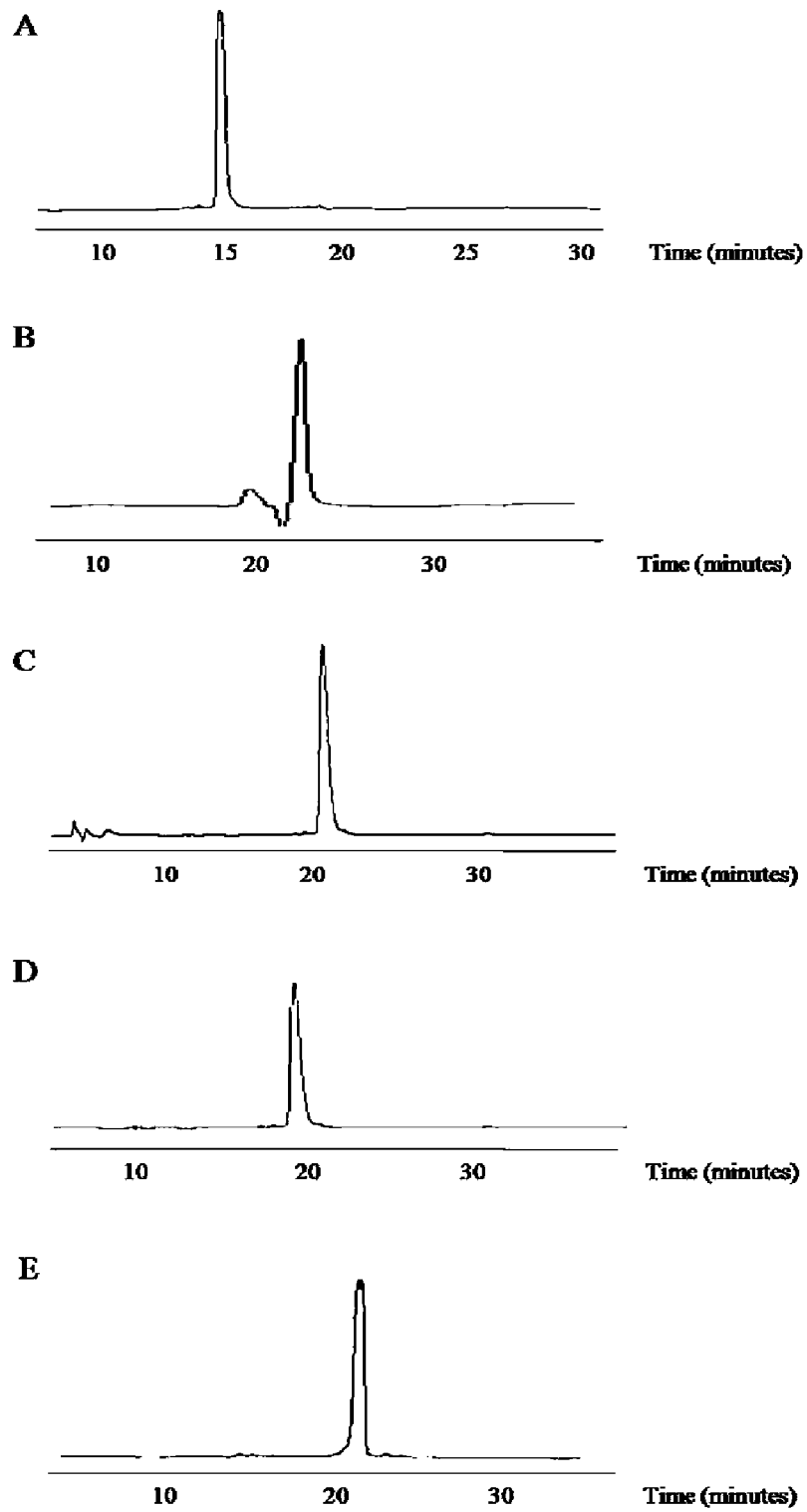

FIG. 7 shows the reverse phase chromatography results to compare purification folds and structural differences of brazzein variants according to the present invention.
A: Purified minor-type brazzein
B: Purified quaternary brazzein variant (29-ins30 Lys_H30R_E35D_E40A)
C: Purified quaternary brazzein variant (29-ins30 Lys_H30R_E35D_E40D)
D: Purified quaternary brazzein variant (29-ins30 Lys_H30R_E35D_E40K)
E: Purified quaternary brazzein variant (29-ins30 Lys_H30R_E35D_E40R)

DETAILED DESCRIPTION OF EXEMPLARY EMBODIMENTS

As described above, the brazzein variant according to the present invention has excellent properties such as thermal stability, acid resistance and water solubility compared to a conventional brazzein and also shows higher sweetness at least 2 times and up to 3.3 times that of the conventional brazzein. Like the brazzein variant, the brazzein multi-variant according to the present invention also has the same stability as the minor-type brazzein protein and shows higher sweetness at least 4 times and up to 20 times that of the minor-type brazzein protein. Therefore, the brazzein variant according to the present invention may be widely used as a sweetener in food compositions since a greater amount of other sweeteners may be replaced with a smaller amount of the brazzein variant.

Hereinafter, exemplary embodiments of the present invention will be described in detail.

However, the present invention is not limited to the embodiments disclosed below, but can be implemented in various forms. The following embodiments are described in order to enable those of ordinary skill in the art to embody and practice the present invention.

Example 1

Cloning of Polynucleotide Coding for Primary Brazzein Variant

In order to prepare a brazzein variant having higher sweetness than a wild-type brazzein protein, first, one certain amino acid of an amino acid sequence of a minor-type brazzein protein was selected and exchanged into another certain amino acid.

First, external amino acid residues (side chain) of brazzein facing outwards and having polarity were selected as the certain amino acid to be substituted through structural analysis of the brazzein. Based on this structural information, 40 primers having complementary sequences to the forward primers as listed in the following Table 1 were constructed so that a minor-type brazzein protein could be synthesized in *E. coli* used in Korean Patent Application No. 2006-97619 filed by the same applicant as the present invention using a recombinant expression vector (pET26B(+)-Brzzein(Met-), see Example 6) as a template. Here, the recombinant expression vector has a sequence set forth in SEQ ID NO: 1 from which an unnecessary "ATG" sequence is removed. The forward and reverse primers were designed in consideration of the length of electrical properties of external amino acid residues of a certain amino acid sequence of the minor-type brazzein protein (see Table 1). A total of 40 expression vectors, each of which includes a nucleotide sequence coding for a brazzein variant, were constructed by substituting certain positions of the minor-type brazzein protein according to the manufacturer's guide using the primers listed in the following Table 1 and a QuikChange™ site-directed mutagenesis kit (Stratagene, USA). In this case, the underlined regions in the primer sequences listed in the following Table 1 represent sequences modified for preparation of brazzein variants.

TABLE 1

Primers used to construct primary brazzein variants

| Positions | Amino acid residues before mutation | Amino acid residues after mutation | Primers used | Before Mutation | After Mutation | Sequence Nos. |
|---|---|---|---|---|---|---|
| 5 | Lys (K) | Ala (A) | tgc aaa gct gtt tac | positive | neutral | SEQ ID NO: 2 |
|  |  | Asp (D) | tgc aaa gac gtt tac |  | negative | SEQ ID NO: 3 |
|  |  | Glu (E) | tgc aaa gaa gtt tac |  | negative | SEQ ID NO: 4 |
|  |  | His (H) | tgc aaa cac gtt tac |  | positive | SEQ ID NO: 5 |
|  |  | Arg (R) | tgc aaa cgt gtt tac |  | positive | SEQ ID NO: 6 |

TABLE 1-continued

Primers used to construct primary brazzein variants

| Positions | Amino acid residues before mutation | Amino acid residues after mutation | Primers used | Before Mutation | After Mutation | Sequence Nos. |
|---|---|---|---|---|---|---|
| 28 | Asp (D) | Ala (A) | aag ctt gct aag cat | negative | neutral | SEQ ID NO: 7 |
|  |  | His (H) | aag ctt cac aag cat |  | positive | SEQ ID NO: 8 |
|  |  | Lys (K) | aag ctt aaa aag cat |  | positive | SEQ ID NO: 9 |
|  |  | Arg (R) | aag ctt cgt aag cat |  | positive | SEQ ID NO: 10 |
|  |  | Glu (E) | aag ctt gaa aag cat |  | negative | SEQ ID NO: 11 |
| 29 | Lys (K) | Ala (A) | ctt gat gct cat gct | positive | neutral | SEQ ID NO: 12 |
|  |  | Arg (R) | ctt gat cgt cat gct |  | positive | SEQ ID NO: 13 |
|  |  | His (H) | ctt gat cgc cat gct |  | positive | SEQ ID NO: 14 |
|  |  | Asp (D) | ctt gat gac cat gct |  | negative | SEQ ID NO: 15 |
|  |  | Glu (E) | ctt gat gaa cat gct |  | negative | SEQ ID NO: 16 |
| 30 | His (H) | Ala (A) | gat aag gct gct cga | positive | neutral | SEQ ID NO: 17 |
|  |  | Lys (K) | gat aag aaa gct cga |  | positive | SEQ ID NO: 18 |
|  |  | Arg (R) | gat aag cgt gct cga |  | positive | SEQ ID NO: 19 |
|  |  | Asp (D) | gat aag gac gct cga |  | negative | SEQ ID NO: 20 |
|  |  | Glu (E) | gat aag gaa gct cga |  | negative | SEQ ID NO: 21 |
| 32 | Arg (R) | Ala (A) | cat gct gct tct gga | positive | neutral | SEQ ID NO: 22 |
|  |  | Lys (K) | cat gct aaa tct gga |  | positive | SEQ ID NO: 23 |
|  |  | His (H) | cat gct cac tct gga |  | positive | SEQ ID NO: 24 |
|  |  | Asp (D) | cat gct gac tct gga |  | negative | SEQ ID NO: 25 |
|  |  | Glu (E) | cat gct gaa tct gga |  | negative | SEQ ID NO: 26 |
| 35 | Glu (E) | Ala (A) | tct gga gct tgc ttt | negative | neutral | SEQ ID NO: 27 |
|  |  | Asp (D) | tct gga gac tgc ttt |  | negative | SEQ ID NO: 28 |
|  |  | Lys (K) | tct gga aaa tgc ttt |  | positive | SEQ ID NO: 29 |
|  |  | His (H) | tct gga cac tgc ttt |  | positive | SEQ ID NO: 30 |
|  |  | Arg (R) | tct gga cgt tgc ttt |  | positive | SEQ ID NO: 31 |
| 40 | Glu (E) | Ala (A) | tac gat gct aag aga | negative | neutral | SEQ ID NO: 32 |
|  |  | Asp (D) | tac gat gac aag aga |  | negative | SEQ ID NO: 33 |
|  |  | Lys (K) | tac gat aaa aag aga |  | positive | SEQ ID NO: 34 |
|  |  | His (H) | tac gat cac aag aga |  | positive | SEQ ID NO: 35 |
|  |  | Arg (R) | tac gat cgt aag aga |  | positive | SEQ ID NO: 36 |

TABLE 1-continued

Primers used to construct primary brazzein variants

| Positions | Amino acid residues before mutation | Amino acid residues after mutation | Primers used | Note Before Mutation | After Mutation | Sequence Nos. |
|---|---|---|---|---|---|---|
| 42 | Arg (R) | Ala (A) | gaa aag gct aat ctt | positive | neutral | SEQ ID NO: 37 |
|  |  | Lys (K) | gaa aag aaa aat ctt |  | positive | SEQ ID NO: 38 |
|  |  | His (H) | gaa aag cac aat ctt |  | positive | SEQ ID NO: 39 |
|  |  | Asp (D) | gaa aag gac aat ctt |  | negative | SEQ ID NO: 40 |
|  |  | Glu (E) | gaa aag gaa aat ctt |  | negative | SEQ ID NO: 41 |

More particularly, a polymerase chain reaction (PCR) was performed in a total of 50 μl of a reaction solution containing 10 ng of a pET26B(+)-Brazzein(Met-) vector, a mixture of dNTPs (each having a final concentration of 0.2 mM), 125 ng of each primer listed in Table 1, 5 μl of a 10× reaction buffer, and 1 μl of PfuTurbo DNA polymerase (2.5 U/μl, Stratagene, USA). The PCR reaction was performed by pre-denaturing at 95° C. for 1 minute, followed by 20 cycles of amplification (at 95° C. for 30 seconds; at 55° C. for 60 seconds; and at 68° C. 15 minutes) and one final cycle of extension at 68° C. for 15 minutes. When the PCR reaction was completed, the amplified PCR products were confirmed through 1.0% agarose gel electrophoresis, and then treated with a restriction enzyme DpnI at 37° C. for 1 hour. Immediately after the digestion, a supercompetent cell, *E. coli* XL1-Blue, was transformed with the amplified PCR products. The transformed XL1-Blue strain was cultured for 12 hours in an LB-agar plate containing 50 μg/ml kanamycin to screen antibiotic-resistant colonies. Then, the screened colonies were incubated in an LB-agar medium to isolate full-length DNA from *E. coli*. The genetic analysis indicated that a nucleotide sequence coding for each brazzein variant was limited to a pelB signal sequence in the case of the isolated DNA. These were represented by sequence numbers, and given nucleotide names, as listed in the following Table 2 which will described later, for example, the term "K5D" means that a lysine residue at position 5 of a minor-type brazzein protein is substituted with an aspartic acid residue. A one-letter code representing each amino acid was designated according to the known amino acid code.

TABLE 2

Names and sequence numbers of polynucleotides coding for primary brazzein variants

| Positions of amino acids in primary brazzein variants | Names of nucleotides coding for primary brazzein variants | Sequence Nos. |
|---|---|---|
| K5A | *E. coli* pelB + Brazzein(K5A) gene | SEQ ID NO: 42 |
| K5D | *E. coli* pelB + Brazzein(K5D) gene | SEQ ID NO: 43 |
| K5E | *E. coli* pelB + Brazzein(K5E) gene | SEQ ID NO: 44 |
| K5H | *E. coli* pelB + Brazzein(K5H) gene | SEQ ID NO: 45 |
| K5R | *E. coli* pelB + Brazzein(K5R) gene | SEQ ID NO: 46 |
| D28A | *E. coli* pelB + Brazzein(D28A) gene | SEQ ID NO: 47 |
| D28H | *E. coli* pelB + Brazzein(D28H) gene | SEQ ID NO: 48 |
| D28K | *E. coli* pelB + Brazzein(D28K) gene | SEQ ID NO: 49 |
| D28R | *E. coli* pelB + Brazzein(D28R) gene | SEQ ID NO: 50 |

TABLE 2-continued

Names and sequence numbers of polynucleotides coding for primary brazzein variants

| Positions of amino acids in primary brazzein variants | Names of nucleotides coding for primary brazzein variants | Sequence Nos. |
|---|---|---|
| D28E | *E. coli* pelB + Brazzein(D28E) gene | SEQ ID NO: 51 |
| K29A | *E. coli* pelB + Brazzein(K29A) gene | SEQ ID NO: 52 |
| K29R | *E. coli* pelB + Brazzein(K29R) gene | SEQ ID NO: 53 |
| K29H | *E. coli* pelB + Brazzein(K29H) gene | SEQ ID NO: 54 |
| K29D | *E. coli* pelB + Brazzein(K29D) gene | SEQ ID NO: 55 |
| K29E | *E. coli* pelB + Brazzein(K29E) gene | SEQ ID NO: 56 |
| H30A | *E. coli* pelB + Brazzein(H30A) gene | SEQ ID NO: 57 |
| H30K | *E. coli* pelB + Brazzein(H30K) gene | SEQ ID NO: 58 |
| H30R | *E. coli* pelB + Brazzein(H30R) gene | SEQ ID NO: 59 |
| H30D | *E. coli* pelB + Brazzein(H30D) gene | SEQ ID NO: 60 |
| H30E | *E. coli* pelB + Brazzein(H30E) gene | SEQ ID NO: 61 |
| R32A | *E. coli* pelB + Brazzein(R32A) gene | SEQ ID NO: 62 |
| R32K | *E. coli* pelB + Brazzein(R32K) gene | SEQ ID NO: 63 |
| R32H | *E. coli* pelB + Brazzein(R32H) gene | SEQ ID NO: 64 |
| R32D | *E. coli* pelB + Brazzein(R32D) gene | SEQ ID NO: 65 |
| R32E | *E. coli* pelB + Brazzein(R32E) gene | SEQ ID NO: 66 |
| E35A | *E. coli* pelB + Brazzein(E35A) gene | SEQ ID NO: 67 |
| E35D | *E. coli* pelB + Brazzein(E35D) gene | SEQ ID NO: 68 |
| E35K | *E. coli* pelB + Brazzein(E35K) gene | SEQ ID NO: 69 |
| E35H | *E. coli* pelB + Brazzein(E35H) gene | SEQ ID NO: 70 |
| E35R | *E. coli* pelB + Brazzein(E35R) gene | SEQ ID NO: 71 |
| E40A | *E. coli* pelB + Brazzein(E40A) gene | SEQ ID NO: 72 |
| E40D | *E. coli* pelB + Brazzein(E40D) gene | SEQ ID NO: 73 |
| E40K | *E. coli* pelB + Brazzein(E40K) gene | SEQ ID NO: 74 |
| E40H | *E. coli* pelB + Brazzein(E40H) gene | SEQ ID NO: 75 |
| E40R | *E. coli* pelB + Brazzein(E40R) gene | SEQ ID NO: 76 |
| R42A | *E. coli* pelB + Brazzein(R42A) gene | SEQ ID NO: 77 |
| R42K | *E. coli* pelB + Brazzein(R42K) gene | SEQ ID NO: 78 |
| R42H | *E. coli* pelB + Brazzein(R42H) gene | SEQ ID NO: 79 |
| R42D | *E. coli* pelB + Brazzein(R42D) gene | SEQ ID NO: 80 |
| R42E | *E. coli* pelB + Brazzein(R42E) gene | SEQ ID NO: 81 |

Figure 1:
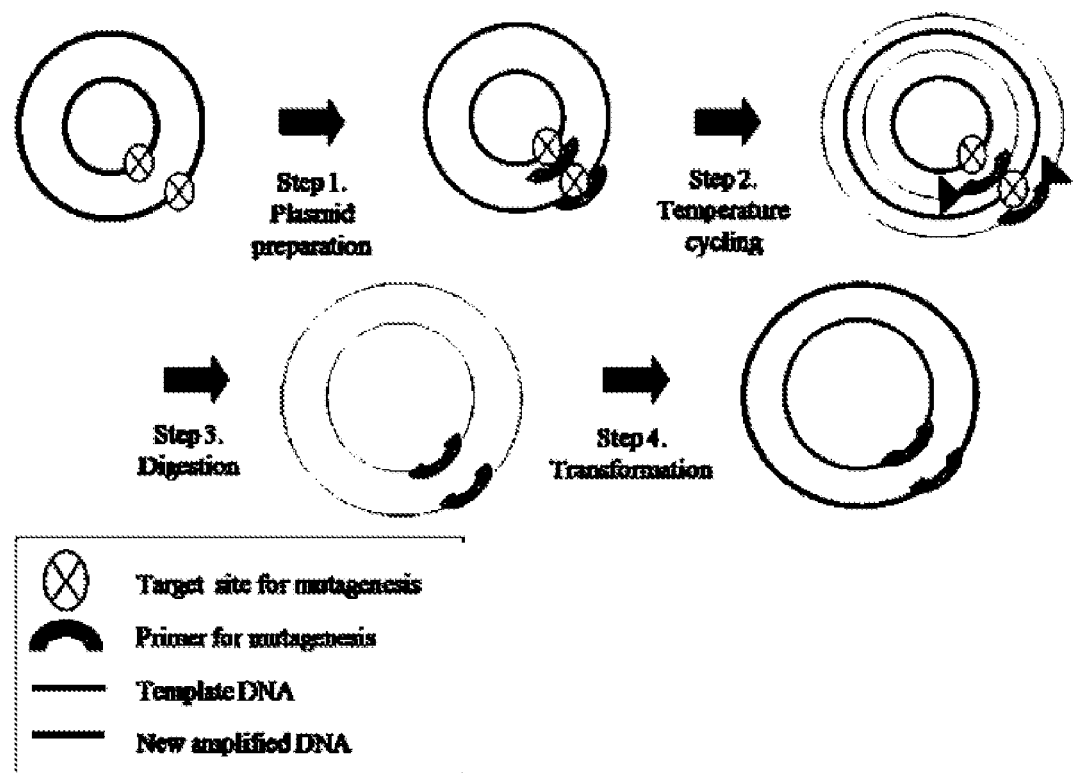
FIG. 1 is a schematic diagram illustrating a process for constructing a recombinant expression vector so as to express a brazzein variant according to the present invention.

From the experiment results, it was confirmed that all kinds of the expression vectors for brazzein variants were constructed, and *E. coli* BL21(star) was transformed with each of the expression vectors and used to mass-express the brazzein variant (see FIG. 1).

Example 2

Expression and Purification of Primary Brazzein Variant 2-1. Expression of Primary Brazzein Variant Each of the *E. coli* BL21(star) strains obtained by introducing 32 expression vectors for primary brazzein variants prepared in Example 1 was incubated in 1 l of an LB medium supplemented with 30 μl/ml kanamycin at 37° C. for 12 hours without adding a protein inducer, isopropyl β-D-thoigalactopyranoside (IPTG) to express each brazzein variant in each transformed E. coli strain.

2-2. Purification of Brazzein Variant

Each E. coli strain incubated in Example 2-1 was collected by centrifugation at 8,000 g for 10 minutes. After the collection, the E. coli strain was suspended in a 30 mM Tri-HCl (pH 8.0) solution including 20% sucrose, and a 0.5 M EDTA (pH 8.0) solution was added so that its final concentration could account for 1 mM, and slowly stirred at room temperature for 10 minutes. The resulting reaction solution was centrifuged at 10,000 g and 4° C. for 10 minutes, and a supernatant was removed. Then, cold 5 mM $MgSO_4$ was added, and slowly stirred on ice for 10 minutes. In this procedure, periplasmic proteins were separated from a buffered solution. Thereafter, the resulting mixture was centrifuged at 10,000 g and 4° C. for 10 minutes to separate a pallet and a supernatant, and the pallet was heat-treated at 80° C. for 30 minutes to purify a brazzein variant present in the periplasm. Then, the brazzein variant was dialyzed in distilled water for 24 hours, and freeze-dried to obtain a purified primary brazzein variant represented by each sequence number as listed in the following Table 3. Also, a purification fold of the primary brazzein variant was primarily confirmed through SDS-PAGE.

TABLE 3

Names and sequence numbers of primary brazzein variants

| Positions of amino acids in primary brazzein variants | Brazzein variant names | Sequence Nos. |
|---|---|---|
| — | Brazzein(minor type) | SEQ ID NO: 82 |
| K5A | Brazzein(K5A) | SEQ ID NO: 83 |
| K5D | Brazzein(K5D) | SEQ ID NO: 84 |
| K5E | Brazzein(K5E) | SEQ ID NO: 85 |
| K5H | Brazzein(K5H) | SEQ ID NO: 86 |
| K5R | Brazzein(K5R) | SEQ ID NO: 87 |
| D28A | Brazzein(D28A) | SEQ ID NO: 88 |
| D28H | Brazzein(D28H) | SEQ ID NO: 89 |
| D28K | Brazzein(D28K) | SEQ ID NO: 90 |
| D28R | Brazzein(D28R) | SEQ ID NO: 91 |
| D28E | Brazzein(D28E) | SEQ ID NO: 92 |
| K29A | Brazzein(K29A) | SEQ ID NO: 93 |
| K29R | Brazzein(K29R) | SEQ ID NO: 94 |
| K29H | Brazzein(K29H) | SEQ ID NO: 95 |
| K29D | Brazzein(K29D) | SEQ ID NO: 96 |
| K29E | Brazzein(K29E) | SEQ ID NO: 97 |
| H30A | Brazzein(H30A) | SEQ ID NO: 98 |
| H30K | Brazzein(H30K) | SEQ ID NO: 99 |
| H30R | Brazzein(H30R) | SEQ ID NO: 100 |
| H30D | Brazzein(H30D) | SEQ ID NO: 101 |
| H30E | Brazzein(H30E) | SEQ ID NO: 102 |
| R32A | Brazzein(R32A) | SEQ ID NO: 103 |
| R32K | Brazzein(R32K) | SEQ ID NO: 104 |
| R32H | Brazzein(R32H) | SEQ ID NO: 105 |
| R32D | Brazzein(R32D) | SEQ ID NO: 106 |
| R32E | Brazzein(R32E) | SEQ ID NO: 107 |
| E35A | Brazzein(E35A) | SEQ ID NO: 108 |
| E35D | Brazzein(E35D) | SEQ ID NO: 109 |
| E35K | Brazzein(E35K) | SEQ ID NO: 110 |
| E35H | Brazzein(E35H) | SEQ ID NO: 111 |
| E35R | Brazzein(E35R) | SEQ ID NO: 112 |
| E40A | Brazzein(E40A) | SEQ ID NO: 113 |
| E40D | Brazzein(E40D) | SEQ ID NO: 114 |
| E40K | Brazzein(E40K) | SEQ ID NO: 115 |
| E40H | Brazzein(E40H) | SEQ ID NO: 116 |
| E40R | Brazzein(E40R) | SEQ ID NO: 117 |
| R42A | Brazzein(R42A) | SEQ ID NO: 118 |

TABLE 3-continued

Names and sequence numbers of primary brazzein variants

| Positions of amino acids in primary brazzein variants | Brazzein variant names | Sequence Nos. |
|---|---|---|
| R42K | Brazzein(R42K) | SEQ ID NO: 119 |
| R42H | Brazzein(R42H) | SEQ ID NO: 120 |
| R42D | Brazzein(R42D) | SEQ ID NO: 121 |
| R42E | Brazzein(R42E) | SEQ ID NO: 122 |

From the experiment results, it was confirmed that the brazzein proteins were purified with high purity, and had a molecular weight of approximately 6.5 kDa.

2-3. Confirmation of Purification Folds and Structural Changes of Primary Brazzein Variants In order to analyze the structural difference of the purified minor-type brazzein protein and the respective brazzein variants purified in Example 2-2 after confirmation of the purification folds, the analysis was performed using high performance liquid chromatography (Varina) and a reverse-phase chromatography column (Vydac 214TP54, USA). A solvent condition was set as follows. Solvent A in which 0.05% trifluoroacetic acid was included in water and solvent B in which 0.05% trifluoroacetic acid was included in acetonitrile were eluted at a flow rate of 1 ml/minute for 30 minutes so that solvent B could flow in a linear gradient from 10% to 50%. The eluted solution was observed for a change in absorbance at 210 nm.

As a result, it was confirmed that the most brazzein variants were eluted after a retention time of 15 minutes, which indicates that there is hardly any change in structural difference of the expressed brazzein variants.

Example 3

Measurement of Activities (Sweetness) and Thermal Stabilities of Primary Brazzein Variants 3-1. Measurement of Sweetness of Primary Brazzein Variants Since the recombinant brazzein according to the present invention is not a sucrose-based compound having a cyclic ring, the sweetness of the recombinant brazzein was not measured using a saccharometer. Therefore, the activity of the recombinant brazzein was measured using the human sense of taste. Sugar content measurement was performed on 20 subjects who were trained to feel substantially the same minimum concentration of sucrose in which they could sense sweetness using a sucrose solution. That is, a concentration of each brazzein variant in which the subjects could sense sweetness for the first time was measured. Also, a sweetness ratio of the sucrose solution to the wild-type brazzein was 1 g/100 ml, which was a minimum stimulation level in which the subjects could sense sweetness. Also, a sweetness ratio of the minor-type brazzein protein to the wild-type brazzein was 500 μg/100 ml, which was a minimum stimulation level in which the subjects could sense sweetness. Therefore, the sweetness was calculated using the sweetness ratios (That is, $1/0.0005 = 2000$ for the minor-type brazzein).

TABLE 4

Sweetness test results of respective primary brazzein variants

| Positions of amino acids in primary brazzein variants | Sequence Nos. | Minimum stimulation level in which one senses sweetness for first time (μg/100 ml) | Sweetness ratios of sucrose (1 g/100 ml) to primary brazzein variants (minor-type brazzein: 2000) | Multiples of increased sweetness to minor-type brazzein |
|---|---|---|---|---|
| K5A | SEQ ID NO: 83 | 6,000 | 167 | 0.08 |
| K5D | SEQ ID NO: 84 | 6,000 | 167 | 0.08 |
| K5E | SEQ ID NO: 85 | 6,000 | 167 | 0.08 |
| K5H | SEQ ID NO: 86 | 10,000 | 100 | 0.05 |
| K5R | SEQ ID NO: 87 | 10,000 | 100 | 0.05 |
| D28A | SEQ ID NO: 88 | 10,000 | 100 | 0.05 |
| D28H | SEQ ID NO: 89 | 6,000 | 167 | 0.08 |
| D28K | SEQ ID NO: 90 | 6,000 | 167 | 0.08 |
| D28R | SEQ ID NO: 91 | 6,000 | 167 | 0.08 |
| D28E | SEQ ID NO: 92 | 2,000 | 500 | 0.25 |
| K29A | SEQ ID NO: 93 | 10,000 | 100 | 0.05 |
| K29R | SEQ ID NO: 94 | 10,000 | 100 | 0.05 |
| K29H | SEQ ID NO: 95 | 10,000 | 100 | 0.05 |
| K29D | SEQ ID NO: 96 | 10,000 | 100 | 0.05 |
| K29E | SEQ ID NO: 97 | 10,000 | 100 | 0.05 |
| H30A | SEQ ID NO: 98 | 6,000 | 167 | 0.08 |
| H30K | SEQ ID NO: 99 | 250 | 4,000 | 2 |
| H30R | SEQ ID NO: 100 | 150 | 6,600 | 3.3 |
| H30D | SEQ ID NO: 101 | 3,000 | 334 | 0.16 |
| H30E | SEQ ID NO: 102 | 3,000 | 334 | 0.16 |
| R32A | SEQ ID NO: 103 | 6,000 | 167 | 0.08 |
| R32K | SEQ ID NO: 104 | 3,000 | 334 | 0.16 |
| R32H | SEQ ID NO: 105 | 3,000 | 334 | 0.16 |
| R32D | SEQ ID NO: 106 | 10,000 | 100 | 0.05 |
| R32E | SEQ ID NO: 107 | 10,000 | 100 | 0.05 |
| E35A | SEQ ID NO: 108 | 10,000 | 100 | 0.05 |
| E35D | SEQ ID NO: 109 | 150 | 6,600 | 3.3 |
| E35K | SEQ ID NO: 110 | 6,000 | 167 | 0.08 |
| E35H | SEQ ID NO: 111 | 6,000 | 167 | 0.08 |
| E35R | SEQ ID NO: 112 | 6,000 | 167 | 0.08 |
| E40A | SEQ ID NO: 113 | 150 | 6,600 | 3.3 |
| E40D | SEQ ID NO: 114 | 150 | 6,600 | 3.3 |
| E40K | SEQ ID NO: 115 | 150 | 6,600 | 3.3 |
| E40H | SEQ ID NO: 116 | 250 | 4,000 | 2 |
| E40R | SEQ ID NO: 117 | 250 | 4,000 | 2 |
| R42A | SEQ ID NO: 118 | 10,000 | 100 | 0.05 |
| R42K | SEQ ID NO: 119 | 3,000 | 334 | 0.16 |
| R42H | SEQ ID NO: 120 | 3,000 | 334 | 0.16 |
| R42D | SEQ ID NO: 121 | 10,000 | 100 | 0.05 |
| R42E | SEQ ID NO: 122 | 10,000 | 100 | 0.05 |

As a result, it was confirmed that the brazzein variants, that is, brazzein(H30K) set forth in SEQ ID NO: 99, brazzein (H30R) set forth in SEQ ID NO: 100, brazzein(E35D) set forth in SEQ ID NO: 109, brazzein(E40A) set forth in SEQ ID NO: 113, brazzein(E40A) set forth in SEQ ID NO: 113, brazzein(E40D) set forth in SEQ ID NO: 114, brazzein (E40K) set forth in SEQ ID NO: 115, brazzein(E40H) set forth in SEQ ID NO: 116 and brazzein(E40R) set forth in SEQ ID NO: 117, had higher sweetness at least 2 times and up to 3.3 times (at least approximately 4,000 times and up to approximately 6,600 times that of 1 g/100 ml sucrose) that of the minor-type brazzein protein, as listed in Table 4. In particular, the brazzein variant (E40D) showed the highest increase in sweetness.

3-2. Measurement of Thermal Stabilities of Primary Brazzein Variants

On the basis of the results measured in Example 3-1, 100 mg of each of the brazzein variants having high sweetness, that is, brazzein(H30K) set forth in SEQ ID NO: 99, brazzein (H30R) set forth in SEQ ID NO: 100, brazzein(E35D) set forth in SEQ ID NO: 109, brazzein(E40A) set forth in SEQ ID NO: 113, brazzein(E40A) set forth in SEQ ID NO: 113, brazzein(E40D) set forth in SEQ ID NO: 114, brazzein (E40K) set forth in SEQ ID NO: 115, brazzein(E40H) set forth in SEQ ID NO: 116 and brazzein(E40R) set forth in SEQ ID NO: 117, was dissolved in a 50 mM Tris-HCl (pH 8.0) solution, and heated at 80° C. for 4 hours. Based on the sweetness measured before the heat treatment of the respective primary brazzein variants, a sweetness change level of each primary brazzein variant was then measured by the 20 subjects in the same manner as in Example 3-1. The sweetness change level was calculated as relative activity, and is shown in FIG. 5.

As a result, it was confirmed that the brazzein variants such as brazzein(H30R) set forth in SEQ ID NO: 100, brazzein (E35D) set forth in SEQ ID NO: 109, brazzein(E40A) set forth in SEQ ID NO: 113, brazzein(E40A) set forth in SEQ ID NO: 113, brazzein(E40D) set forth in SEQ ID NO: 114, brazzein(E40K) set forth in SEQ ID NO: 115 and brazzein (E40R) set forth in SEQ ID NO: 117 maintained their thermal stabilities, as shown in FIG. 5.

Example 4

Cloning of Polynucleotides Coding for Brazzein Multi-Variants

On the basis of the results measured in Example 3-2, secondary brazzein variants having higher sweetness were prepared using the primary brazzein variants (H30R, E35D, E40A, E40D, E40R and E40K) having equivalent stability compared to the minor-type brazzein protein and showing higher sweetness than the minor-type brazzein protein.

More particularly, in order to prepare secondary brazzein variants, a total of 9 polynucleotide sequences coding for secondary brazzein variants were constructed through the site-directed mutagenesis used in Example 1 using the templates listed in the following Tables 5 to 7 (expression vectors including polynucleotide sequences coding for the primary brazzein variants) and the primers used to prepare the primary brazzein variants. In the nomenclature of the templates listed in the following Tables 5 to 7, for example, the term "H30R_E35D" means that a histidine residue at position 30 of a minor-type brazzein protein is substituted with an arginine residue and a glutamic acid residue at position 35 of the minor-type brazzein protein is also substituted with an aspartic acid residue, and the term "29ins30 Lys_" means that a lysine residue is inserted between positions 29 and 30 of the minor-type brazzein protein. Also, the underlined regions in the primer sequences refer to sequences modified for preparation of brazzein variants.

TABLE 5

Templates and primers used to prepare secondary brazzein variants

| Templates used to prepare secondary brazzein variants (Sequence Nos.) | Primer used to prepare secondary brazzein variants | | Secondary brazzein variants prepared |
|---|---|---|---|
| | Primer sequence | Sequence Nos. | |
| E. coli pelB + Brazzein(H30R) gene (SEQ ID NO: 59) | tct gga gac tgc ttt | SEQ ID NO: 28 | H30R_E35D |
| | tac gat gct aag aga | SEQ ID NO: 32 | H30R_E40A |
| | tac gat gac aag aga | SEQ ID NO: 33 | H30R_E40D |
| | tac gat aaa aag aga | SEQ ID NO: 34 | H30R_E40K |
| | tac gat cgt aag aga | SEQ ID NO: 36 | H30R_E40R |
| E. coli pelB + Brazzein(E35D) gene (SEQ ID NO: 68) | tac gat gct aag aga | SEQ ID NO: 32 | E35D_E40A |
| | tac gat gac aag aga | SEQ ID NO: 33 | E35D_E40D |
| | tac gat aaa aag aga | SEQ ID NO: 34 | E35D_E40K |
| | tac gat cgt aag aga | SEQ ID NO: 36 | E35D_E40R |

TABLE 6

Templates and primers used to prepare tertiary brazzein variants

| Templates used to prepare tertiary brazzein variants (Sequence Nos.) | Primer used to prepare tertiary brazzein variants | | Tertiary brazzein variants prepared |
|---|---|---|---|
| | Primer sequences | Sequence Nos. | |
| E. coli pelB + Brazzein(H30R_E35D) gene (SEQ ID NO: 123) | tac gat gct aag aga | SEQ ID NO: 32 | H30R_E35D_E40A |
| | tac gat gac aag aga | SEQ ID NO: 33 | H30R_E35D_E40D |
| | tac gat aaa aag aga | SEQ ID NO: 34 | H30R_E35D_E40K |
| | tac gat cgt aag aga | SEQ ID NO: 36 | H30R_E35D_E40R |

TABLE 7

Templates and primers used to prepare quaternary brazzein variants

| Templates used to prepare quaternary brazzein variants (Sequence Nos.) | Primer used to prepare quaternary brazzein variants | | Quaternary brazzein variants prepared |
|---|---|---|---|
| | Primer sequences | Sequence Nos. | |
| E. coli pelB + Brazzein(H30R_E35D_E40A) gene (SEQ ID NO: 132) | Gataagaaacatgct | SEQ ID NO: 136 | 29ins30 Lys_H30R_E35D_E40A |
| E. coli pelB + Brazzein(H30R_E35D_E40D) gene (SEQ ID NO: 133) | Gataagaaacatgct | SEQ ID NO: 136 | 29ins30 Lys_H30R_E35D_E40D |
| E. coli pelB + Brazzein(H30R_E35D_E40K) gene (SEQ ID NO: 134) | Gataagaaacatgct | SEQ ID NO: 136 | 29ins30 Lys_H30R_E35D_E40K |
| E. coli pelB + Brazzein(H30R_E35D_E40R) gene (SEQ ID NO: 135) | Gataagaaacatgct | SEQ ID NO: 136 | 29ins30 Lys_H30R_E35D_E40R |

In order to prepare tertiary brazzein variants showing higher sweetness, a total of 4 polynucleotide sequences coding for tertiary brazzein variants were constructed through the site-directed mutagenesis used in Example 1 using the templates listed in Table 5 (expression vectors including polynucleotide sequences coding for the secondary brazzein variants) and the primers used to prepare the primary brazzein variants.

On the assumption that the lysine and histidine residues at positions 29 and 30 of the minor-type brazzein protein are important in conferring sweet taste through the sweetness test results of the primary brazzein variants described in Example 3, a lysine residue was inserted between the positions 29 and 30 of the tertiary brazzein variants to prepare quaternary brazzein variants. For this purpose, the templates listed in Table 5 (expression vectors including polynucleotide sequences coding for the tertiary brazzein variants) and primers including bases coding for a lysine residue as set forth in SEQ ID NO: 136 were synthesized, and a total of 4 polynucleotide sequences coding for quaternary brazzein variants were constructed through the site-directed mutagenesis used in Example 1. These were represented by sequence numbers, and given nucleotide names, as listed in the following Table 8.

As a result, a total of 17 expression vectors for expression of brazzein multi-variants were constructed, and E. coli BL21 (star) was transformed with each of the expression vectors and used to mass-express the brazzein variants.

TABLE 8

Nomenclatures and sequence numbers of polynucleotides coding for brazzein multi-variants

| Positions of amino acids in brazzein multi-variant | Names of nucleotides coding for brazzein multi-variants | Sequence Nos. |
|---|---|---|
| H30R_E35D | E. coli pelB + Brazzein(H30R_E35D) gene | SEQ ID NO: 123 |
| H30R_E40A | E. coli pelB + Brazzein(H30R_E40A) gene | SEQ ID NO: 124 |
| H30R_E40D | E. coli pelB + Brazzein(H30R_E40D) gene | SEQ ID NO: 125 |
| H30R_E40K | E. coli pelB + Brazzein(H30R_E40K) gene | SEQ ID NO: 126 |
| H30R_E40R | E. coli pelB + Brazzein(H30R_E40R) gene | SEQ ID NO: 127 |
| E35D_E40A | E. coli pelB + Brazzein(E35D_E40A) gene | SEQ ID NO: 128 |
| E35D_E40D | E. coli pelB + Brazzein(E35D_E40D) gene | SEQ ID NO: 129 |
| E35D_E40K | E. coli pelB + Brazzein(E35D_E40K) gene | SEQ ID NO: 130 |
| E35D_E40R | E. coli pelB + Brazzein(E35D_E40R) gene | SEQ ID NO: 131 |
| H30R_E35D_E40A | E. coli pelB + Brazzein(H30R_E35D_E40A) gene | SEQ ID NO: 132 |
| H30R_E35D_E40D | E. coli pelB + Brazzein(H30R_E35D_E40D) gene | SEQ ID NO: 133 |
| H30R_E35D_E40K | E. coli pelB + Brazzein(H30R_E35D_E40K) gene | SEQ ID NO: 134 |
| H30R_E35D_E40R | E. coli pelB + Brazzein(H30R_E35D_E40R) gene | SEQ ID NO: 135 |
| 29ins30 Lys_H30R_E35D_E40A | E. coli pelB + Brazzein(29ins30 Lys_H30R_E35D_E40A) gene | SEQ ID NO: 138 |
| 29ins30 Lys_H30R_E35D_E40D | E. coli pelB + Brazzein(29ins30 Lys_H30R_E35D_E40D) gene | SEQ ID NO: 139 |
| 29ins30 Lys_H30R_E35D_E40K | E. coli pelB + Brazzein(29ins30 Lys_H30R_E35D_E40K) gene | SEQ ID NO: 140 |
| 29ins30 Lys_H30R_E35D_E40R | E. coli pelB + Brazzein(29ins30 Lys_H30R_E35D_E40R) gene | SEQ ID NO: 141 |

Example 5

Expression, Purification and Characterization of Brazzein Multi-Variants

Purified brazzein multi-variants represented by sequence numbers listed in Tables 9 to 11 were expressed and purified in the same manner as in Examples 2-1 and 2-2 using E. coli BL21(star) obtained by introducing each of the 17 expression vectors for expression of the brazzein multi-variants prepared in Example 4. Then, the purification folds of the brazzein multi-variants were primarily confirmed through SDS-PAGE.

TABLE 9

Names and sequence numbers of secondary brazzein variants

| Positions of amino acids in secondary brazzein variants | Secondary brazzein variant names | Sequence Nos. |
|---|---|---|
| H30R_E35D | Brazzein(H30R_E35D) | SEQ ID NO: 142 |
| H30R_E40A | Brazzein(H30R_E40A) | SEQ ID NO: 143 |
| H30R_E40D | Brazzein(H30R_E40D) | SEQ ID NO: 144 |
| H30R_E40K | Brazzein(H30R_E40K) | SEQ ID NO: 145 |
| H30R_E40R | Brazzein(H30R_E40R) | SEQ ID NO: 146 |
| E35D_E40A | Brazzein(E35D_E40A) | SEQ ID NO: 147 |
| E35D_E40D | Brazzein(E35D_E40D) | SEQ ID NO: 148 |
| E35D_E40K | Brazzein(E35D_E40K) | SEQ ID NO: 149 |
| E35D_E40R | Brazzein(E35D_E40R) | SEQ ID NO: 150 |

TABLE 10

Names and sequence numbers of tertiary brazzein variants

| Positions of amino acids in tertiary brazzein variant | Tertiary brazzein variant names | Sequence Nos. |
|---|---|---|
| H30R_E35D_E40A | Brazzein(H30R_E35D_E40A) | SEQ ID NO: 151 |
| H30R_E35D_E40D | Brazzein(H30R_E35D_E40D) | SEQ ID NO: 152 |
| H30R_E35D_E40K | Brazzein(H30R_E35D_E40K) | SEQ ID NO: 153 |
| H30R_E35D_E40R | Brazzein(H30R_E35D_E40R) | SEQ ID NO: 154 |

TABLE 11

Names and sequence numbers of quaternary brazzein variants

| Positions of amino acids in quaternary brazzein variants | Quaternary brazzein variant names | Sequence Nos. |
|---|---|---|
| 29ins30 Lys_H30R_E35D_E40A | Brazzein(29ins30 Lys_H30R_E35D_E40A) | SEQ ID NO: 155 |
| 29ins30 Lys_H30R_E35D_E40D | Brazzein(29ins30 Lys_H30R_E35D_E40D) | SEQ ID NO: 156 |
| 29ins30 Lys_H30R_E35D_E40K | Brazzein(29ins30 Lys_H30R_E35D_E40K) | SEQ ID NO: 157 |
| 29ins30 Lys_H30R_E35D_E40R | Brazzein(29ins30 Lys_H30R_E35D_E40R) | SEQ ID NO: 158 |

As a result, it was seen that the brazzein proteins were purified with high purity, and had a molecular weight of approximately 6.5 kDa, as shown in FIG. 6.

Also, the structural differences in the brazzein multi-variants were analyzed in the same manner as in Example 2-3 using high performance liquid chromatography (Varina). As a result, it was confirmed that the most brazzein multi-variants except for the quaternary brazzein variants were eluted after a retention time of 15 minutes, which was identical to those of the brazzein variants. However, it was confirmed that the quaternary brazzein variants were eluted after a retention time of approximately 20 minutes. From these results, it was seen that the structural difference from the wild-type brazzein protein was caused as the lysine residue was inserted between the lysine residue and the arginine residue at positions 29 and 30 of the tertiary brazzein variant (see FIG. 7).

Also, the brazzein multi-variants were measured for activity (sweetness) in the same manner as in Example 3-1. The measurement results are listed in the following Table 12.

TABLE 12

Test results of sweetness of brazzein multi-variants

| Kind of multi-variants Positions of amino acid in variants (Sequence Nos.) | Minimum stimulation level in which one senses sweetness for first time (µg/ml) | Sweetness ratios of sucrose (1 g/100 ml) to brazzein multi-variants | Multiples of increased sweetness to minor-type brazzein |
|---|---|---|---|
| Secondary variants | | | |
| H30R_E35D (SEQ ID NO: 142) | 1,250 | 8,000 | 4 |
| H30R_E40A (SEQ ID NO: 143) | 1,250 | 8,000 | 4 |
| H30R_E40D (SEQ ID NO: 144) | 1,250 | 8,000 | 4 |
| H30R_E40K (SEQ ID NO: 145) | 1,000 | 10,000 | 5 |
| H30R_E40R (SEQ ID NO: 146) | 1,000 | 10,000 | 5 |
| E35D_E40A (SEQ ID NO: 147) | 1,000 | 10,000 | 5 |
| E35D_E40D (SEQ ID NO: 148) | 1,000 | 10,000 | 5 |
| E35D_E40K (SEQ ID NO: 149) | 1,250 | 8,000 | 4 |
| E35D_E40R (SEQ ID NO: 150) | 850 | 12,000 | 6 |
| Tertiary variant | | | |
| H30R_E35D_E40A (SEQ ID NO: 151) | 650 | 15,000 | 7.5 |
| H30R_E35D_E40D (SEQ ID NO: 152) | 500 | 20,000 | 10 |
| H30R_E35D_E40K (SEQ ID NO: 153) | 500 | 20,000 | 10 |
| H30R_E35D_E40R (SEQ ID NO: 154) | 450 | 22,000 | 11 |
| Quaternary variant | | | |
| 29ins30 Lys_H30R_E35D_E40A (SEQ ID NO: 155) | 400 | 25,000 | 12.5 |
| 29ins30 Lys_H30R_E35D_E40D (SEQ ID NO: 156) | 350 | 28,000 | 14 |
| 29ins30 Lys_H30R_E35D_E40K (SEQ ID NO: 157) | 350 | 28,000 | 14 |
| 29ins30 Lys_H30R_E35D_E40R (SEQ ID NO: 158) | 250 | 40,000 | 20 |

As listed in Table 12, it was seen that all the brazzein multi-variants had higher sweetness at least 4 times and up to approximately 20 times (at least approximately 8,000 times and up to approximately 40,000 times that of 1 g/100 ml sucrose) that of the minor-type brazzein protein.

Also, the brazzein multi-variants were measured for thermal stability in the same manner as in Example 3-2. From these results, it was seen that all the brazzein multi-variants showed the same thermal stability as the minor-type brazzein protein. From the high performance liquid chromatography analysis of the quaternary variants out of the brazzein multi-variants, it was confirmed that the quaternary variants maintained their constant thermal stability in spite of the fact that the quaternary variants had different structural properties than the minor-type brazzein protein.

In summary, the external amino acid residues of the brazzein protein facing outwards and having polarity were selected through the structure and amino acid sequence of the minor-type brazzein protein to prepare 40 primary brazzein variants. Then, the 6 primary brazzein variants (H30R, E35D, E40A, E40D, E40R and E40K), which had equivalent thermal stability and showed higher sweetness at least 2 times and up to 3.3 times that of the minor-type brazzein protein, were selected from the primary brazzein variants. The brazzein multi-variants showing equivalent thermal stability and higher sweetness compared to the minor-type brazzein protein were prepared using the selected primary brazzein variants. Except for the quaternary brazzein variants in which a lysine residue was inserted between a lysine residue and an arginine residue at positions 29 and 30 of the tertiary brazzein variant, the most brazzein multi-variants had the same structure as the minor-type brazzein protein. The structural difference in the quaternary brazzein variants was considered to be affected by the inserted lysine residue. However, all the brazzein multi-variants including the quaternary brazzein variants showed the same thermal stability as the minor-type brazzein protein, and had increased sweetness at least 4 times and up to 40 times that of the minor-type brazzein protein.

Example 6

Construction of Recombinant Expression Vector pET26B(+)-Brazzein(Met-)

6-1. Synthesis of Novel Artificial Gene Coding for Brazzein

On the basis of the amino acid sequence except for the first amino acid (pyroglutamic acid) in the amino acid sequence (Genbank Accession No. P56552) of brazzein obtained from a fruit extract of *Pentadiplandra brazzeana* (Baillon), a sequence set forth in SEQ ID NO: 159 was designed using codons (*E. coli* usage codon) affluent in *E. coli*, as follows. In this case, the bold-faced letters represent bases modified from the sequence of Genbank Accession No. P56552, based on the codons affluent in *E. coli*:

```
GATAAGTGCAAGAAGGTTTACGAAAATTACCCAGTTTCTAAGTGCCAAC

TTGCTAATCAATGCAATTACGATTGCAAGCTTGCTAAGCATGCTAGATC

TGGAGAATGCTTTTACGATGAAAAGAGAAATCTTCAATGCATTTGCGAT

TACTGCGAATACTAA
```

A polynucleotide sequence of a brazzein gene was artificially synthesized by Takara Korea Biomedicals Inc., based on the sequence information of SEQ ID NO: 159.

6-2. Construction of Primers

In order to link each of the synthesized polynucleotide sequences to a pelB signal sequence of pET26B(+) (Novagen, USA), primers were synthesized so that they could include the same restriction enzymes Nco I and Xho I included in a multi-cloning site (MCS) of pET26B(+), and set forth in SEQ ID NO: 160 (forward primer: CATG<u>CCATGG</u>ATAAGTGCAAGAAGGTTTAC) and SEQ ID NO: 161 (reverse primer: CCG<u>CTCGAG</u>TTAGTATTCGCAGTAATCG). Here, the NcoI and XhoI restriction enzyme sites are underlined, respectively.

6-3. Amplification of Brazzein Gene Using PCR

A brazzein gene was amplified using the brazzein gene synthesized in Example 6-1 as a template and the two primers synthesized in Example 6-2. A PCR reaction was carried out in a final volume of 50 µl of a reaction solution including 1.5 µl of a template gene (a synthesized brazzein gene, SEQ ID NO: 159), 2 µl of a forward primer (SEQ ID NO: 160), 1 µl of a reverse primer (SEQ ID NO: 161), 3 µl of 25 mM $MgCl_2$, 4 µl of 2.5 mM dNTP, 5 µl of a 10×Ex-taq buffer, 1 µl of an Ex-taq polymerase (Takara, Japan) and 31.5 µl of $H_2O$. The PCR reaction was performed by pre-denaturing at 94° C. for 2 minutes, followed by 35 cycles of amplification (at 98° C. for 30 seconds; at 58° C. for 2 minutes; and at 74° C. for 3 minutes) and one final cycle of extension at 74° C. for 10 minutes. When the PCR reaction was completed, the amplified brazzein gene was confirmed through 2.0% agarose gel electrophoresis, recovered from the agarose gel, and then extracted and purified using a QIAquick gel extraction kit (Qiagen, USA). The extracted brazzein gene was inserted into a pGEM-T Easy vector (Promega, USA) (which was referred to as pGEM-T Easy-Brazzein), and *E. coli* JM109 was transformed with the brazzein gene-inserted pGEM-T Easy vector. This was incubated in a solid L-broth medium supplemented with 50 µg/ml ampicillin to screen the transformed *E. coli* JM109 strain. Then, the transformed *E. coli* JM109 strain was incubated again in a liquid L-broth medium, and a large amount of the brazzein gene-inserted pGEM-T Easy vector was obtained from the cultured medium.

6-4. Construction of Recombinant Expression Vector pET26B(+)-Brazzein(Met-)

The pGEM-T Easy-Brazzein vector cloned in Example 6-3 was digested with restriction enzymes Nco I and Xho I (using 10×K buffer and 0.1% BSA) at 37° C. for 6 hours. An expression vector pET26B(+) vector containing a T7 promoter was also digested under the same conditions.

A brazzein gene fraction from the pGEM-T Easy-Brazzein vector and the digested pET26B(+) vector were purified using a QIAquick gel extraction kit (Qiagen, USA). The brazzein gene and the pET26B(+) vector were blended, and reacted with T4 DNA ligase (Takara, Japan) at 16° C. for 12 hours. Then, a JM109 supercompetent cell was transformed with the resulting brazzein gene blend (see FIGS. 2 to 4). The recombinant expression vector obtained by the ligation was named pET26B(+)-Brazzein.

Meanwhile, the recombinant brazzein according to the present invention was translocated into the *E. coli* periplasm as the recombinant brazzein was translated after transcription, and a pelB signal sequence fused with the recombinant brazzein was removed by signal peptidase in *E. coli*. However, one amino acid residue Met translated from ATG of the restriction enzyme Nco I present in the primer was not removed by the signal peptidase.

Figure 3:
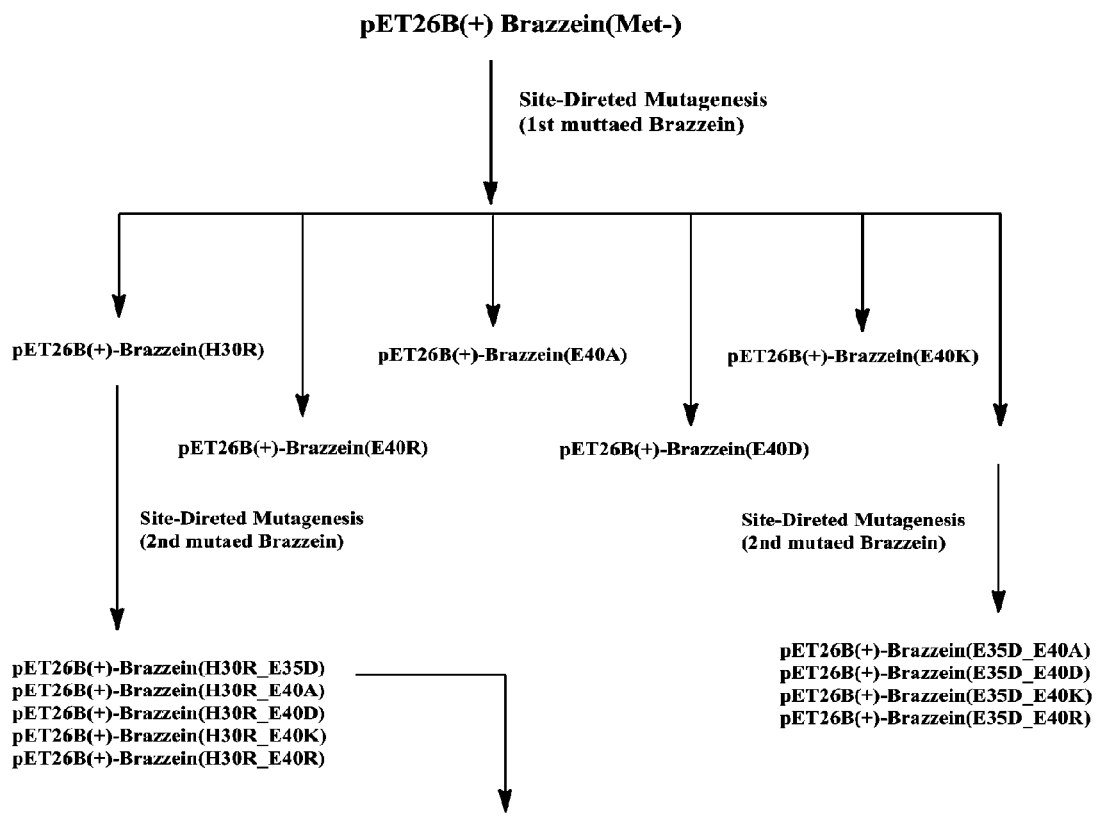

Therefore, in order to express the brazzein as the minor-type brazzein extracted from a natural substance, internal bases "ATG" of the restriction enzyme (Nco I) downstream of the pelB signal sequence were removed from the pET26B(+)-Brazzein vector through the site-directed mutagenesis using PCR (see FIGS. 2 to 4). This procedure will be described in detail, as follows.

The approximately 15 same base pairs (bp) flanking both sides of a base sequence to be deleted from a brazzein gene were designed to synthesize primers set forth in SEQ ID NO: 162 (CAGCCGGCGATGGCCGACAAATGCAAAAAA) and SEQ ID NO: 163 (TTTTTTGCATTTGTCGGC-CATCGCCGGCTG), respectively. The synthesized primers may complementarily bind with single-stranded sequences of brazzein except for ATG to be removed, respectively. An expression vector, pET26B(+)-Brazzein(Met-), in which ATG was removed from the pET26B(+)-Brazzein vector, was obtained according to the manufacturer's guide as described above, by employing a QuikChange™ site-directed mutagenesis kit(Stratagene, USA) using the pET26B(+)-Brazzein vector as a template and primers set forth in SEQ ID NO: 162 and SEQ ID NO: 163. That is, PCR was performed in a total of 50 µl of a reaction solution including 10 ng of a pET26B (+)-Brazzein vector, a mixture of dNTPs (each having a final concentration of 0.2 mM), 125 ng of each of primers set forth in SEQ ID NO: 162 and SEQ ID NO: 163, 5 µl of a 10× reaction buffer and 1 µl of Pfu-Turbo DNA polymerase (2.5 U/µl, Stratagene, USA). The PCR reaction was performed by pre-denaturing at 95° C. for 2 minute, followed by 15 cycles of amplification (at 98° C. for 30 seconds; at 55° C. for 60 seconds; and at 68° C. for 15 minutes) and one final cycle of extension at 68° C. for 10 minutes. When the PCR reaction was completed, the amplified PCR products were confirmed through 1.0% agarose gel electrophoresis, and then treated with a restriction enzyme DpnI at 37° C. for 1 hour. Immediately after the digestion, a supercompetent cell, *E. coli* XL1-Blue, was transformed with the amplified PCR products. The transformed *E. coli* XL1-Blue strain was cultured for 12 hours in an LB-agar plate containing 50 µg/ml kanamycin to screen antibiotic-resistant colonies. Then, the screened colonies were incubated in an LB-agar medium to isolate full-length DNA from *E. coli*. The isolated full-length DNA was subjected to base sequence analysis, and *E. coli* BL21(DE3)-Star was transformed with an expression vector proven to contain an ATG-free brazzein variant, and used to mass-express the brazzein. The recombinant expression vector constructed through the site-directed mutagenesis was named pET26B(+)-Brazzein(Met-).

INDUSTRIAL APPLICABILITY

As described above, the brazzein variant according to the present invention has excellent properties such as thermal stability, acid resistance and water solubility compared to a conventional brazzein and also shows higher sweetness at least 2 times and up to 3.3 times that of the conventional brazzein. Like the brazzein variant, the brazzein multi-variant according to the present invention also has the same stability as the minor-type brazzein protein and shows higher sweetness at least 4 times and up to 20 times that of the minor-type brazzein protein. Therefore, the brazzein variant according to the present invention may be widely used as a sweetener in food compositions since a greater amount of sugar (sucrose) may be replaced with a smaller amount of the brazzein variant.

What is claimed is:

1. A method of preparing a polypeptide comprising a brazzein variant, the method comprising:
   (a) culturing *Escherichia coli* (*E. coli*) transformed with a polynucleotide encoding a polypeptide comprising an *E. coli* pelB signal sequence and a brazzein variant amino acid sequence selected from the group consisting of SEQ ID NO: 142, SEQ ID NO: 151, SEQ ID NO: 152, SEQ ID NO: 153, SEQ ID NO: 154, SEQ ID NO: 155, SEQ ID NO: 156, SEQ ID NO: 157 and SEQ ID NO: 158;
   (b) isolating the polypeptide from the periplasm of the cultured *E. coli*; and
   (c) heat-treating the isolated polypeptide.

2. A brazzein variant having an amino acid sequence selected from the group consisting of SEQ ID NO: 142, SEQ ID NO: 151, SEQ ID NO: 152, SEQ ID NO: 153, SEQ ID NO: 154, SEQ ID NO: 155, SEQ ID NO: 156, SEQ ID NO: 157 and SEQ ID NO: 158.

3. A polynucleotide encoding the brazzein variant of claim 2.

4. The polynucleotide of claim 3, which has a nucleotide sequence selected from the group consisting of SEQ ID NO: 123, SEQ ID NO: 132, SEQ ID NO: 133, SEQ ID NO: 134, SEQ ID NO: 135, SEQ ID NO: 138, SEQ ID NO: 139, SEQ ID NO: 140 and SEQ ID NO: 141.

5. A recombinant expression vector for expression of a brazzein variant comprising:
   a promoter; and
   the polynucleotide of claim 3 operably linked with the promoter.

6. An *E. coli* transformed with the recombinant expression vector of claim 5.

7. A method of preparing a brazzein variant comprising:
   (a) culturing the *E. coli* of claim 6;
   (b) isolating the brazzein variant from the periplasm of the cultured *E. coli*; and
   (c) heat-treating the isolated brazzein variant.

8. A sweetener comprising the brazzein variant of claim 2.

9. A food composition comprising the brazzein variant of claim 2 as a sweetener.

* * * * *